(12) United States Patent
Brinkmann et al.

(10) Patent No.: US 12,193,825 B2
(45) Date of Patent: Jan. 14, 2025

(54) MULTISCALE BRAIN ELECTRODE DEVICES AND METHODS FOR USING THE MULTISCALE BRAIN ELECTRODES

(71) Applicant: Mayo Foundation for Medical Education and Research, Rochester, MN (US)

(72) Inventors: Benjamin H. Brinkmann, Byron, MN (US); Squire Matthew Stead, Bozeman, MT (US); Gregory Worrell, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 220 days.

(21) Appl. No.: 17/544,782

(22) Filed: Dec. 7, 2021

(65) Prior Publication Data
US 2022/0211312 A1    Jul. 7, 2022

Related U.S. Application Data

(63) Continuation of application No. 16/098,335, filed as application No. PCT/US2017/031946 on May 10, 2017, now abandoned.
(Continued)

(51) Int. Cl.
*A61B 5/291* (2021.01)
*A61B 5/00* (2006.01)
(Continued)

(52) U.S. Cl.
CPC ............ *A61B 5/291* (2021.01); *A61B 5/0006* (2013.01); *A61B 5/4064* (2013.01); *A61B 5/4094* (2013.01); *A61B 5/6868* (2013.01); *A61B 5/7264* (2013.01); *A61B 5/053* (2013.01); *A61B 5/055* (2013.01); *A61B 5/4836* (2013.01); *A61B 5/7257* (2013.01); *A61B 5/726* (2013.01); *A61B 5/7282* (2013.01); *A61B 2562/04* (2013.01)

(58) Field of Classification Search
CPC ... A61B 5/0006; A61B 5/4064; A61B 5/4094; A61B 5/24; A61B 5/245; A61B 5/291; A61B 5/6868; A61B 5/7264; A61B 2562/04
See application file for complete search history.

(56) References Cited

U.S. PATENT DOCUMENTS

| | | |
|---|---|---|
| 6,591,138 B1 | 7/2003 | Fischell et al. |
| 7,302,298 B2 | 11/2007 | Lowry et al. |

(Continued)

FOREIGN PATENT DOCUMENTS

WO    WO-2014140432    9/2014

OTHER PUBLICATIONS

EPO Extended European Search Report in European Application No. 17796757.7 dated May 6, 2019, 82 pages.
(Continued)

*Primary Examiner* — Eun Hwa Kim
(74) *Attorney, Agent, or Firm* — Fish & Richardson P.C.

(57) ABSTRACT

Multiscale brain electrodes can be used for spatiotemporal mapping, probing, and therapeutic modulation of the human brain. The applications for such functional mapping and electrical stimulation modulation span, for example, neurological and psychiatric diseases, and brain rehabilitation.

18 Claims, 3 Drawing Sheets

Related U.S. Application Data

(60) Provisional application No. 62/334,843, filed on May 11, 2016.

(51) Int. Cl.
*A61B 5/053* (2021.01)
*A61B 5/055* (2006.01)

(56) References Cited

U.S. PATENT DOCUMENTS

| | | |
|---|---|---|
| 7,463,928 B2 | 12/2008 | Lee et al. |
| 7,941,202 B2 | 5/2011 | Hetke |
| 7,962,219 B2 | 6/2011 | Jaax et al. |
| 7,991,465 B2 | 8/2011 | Bartic |
| 8,150,522 B2 | 4/2012 | Eschauz |
| 8,190,251 B2 | 5/2012 | Molnar et al. |
| 8,447,406 B2 | 5/2013 | Wu et al. |
| 8,774,891 B1 | 7/2014 | Osa et al. |
| 8,855,775 B2 | 10/2014 | Leyde et al. |
| 8,868,172 B2 | 10/2014 | Leyde et al. |
| 8,914,115 B2 | 12/2014 | Giftakis et al. |
| 8,954,144 B2 | 2/2015 | Anderson et al. |
| 9,107,592 B2 | 8/2015 | Litt et al. |
| 9,149,635 B2 | 10/2015 | Denison et al. |
| 9,248,269 B2 | 2/2016 | Kipke et al. |
| 9,409,022 B2 | 8/2016 | Jaax et al. |
| 9,788,744 B2 | 10/2017 | Bland et al. |
| 2005/0203366 A1 | 9/2005 | Donoghue et al. |
| 2008/0027346 A1 | 1/2008 | Litt |
| 2009/0118786 A1 | 5/2009 | Meadows et al. |
| 2009/0234419 A1 | 9/2009 | Machino |
| 2010/0145176 A1 | 6/2010 | Himes |
| 2010/0198297 A1 | 8/2010 | Cogan |
| 2010/0219820 A1 | 9/2010 | Skidmore et al. |
| 2010/0292602 A1* | 11/2010 | Worrell ............ A61B 5/377 607/45 |
| 2011/0208265 A1 | 8/2011 | Erickson |
| 2011/0301665 A1* | 12/2011 | Mercanzini ........ A61B 5/6868 607/45 |
| 2012/0209350 A1 | 8/2012 | Taylor et al. |
| 2012/0245481 A1 | 9/2012 | Blanco |
| 2013/0144365 A1 | 6/2013 | Kipke et al. |
| 2013/0261489 A1 | 10/2013 | Putz |
| 2015/0126829 A1* | 5/2015 | Bernstein ............. A61B 5/05 600/409 |
| 2015/0216437 A1 | 8/2015 | Mihanlovic |
| 2015/0305643 A1 | 10/2015 | Negi et al. |
| 2016/0029916 A1 | 2/2016 | Putz |
| 2016/0120457 A1 | 5/2016 | Wu et al. |
| 2018/0085015 A1 | 3/2018 | Crowder et al. |
| 2019/0150774 A1 | 5/2019 | Brinkmann |

OTHER PUBLICATIONS

International Search Report and Written Opinion for International Application No. PCT/US2017/31946, dated Aug. 11, 2017, 37 pages.
International Preliminary Report on Patentability in International Application. No. PCT/US2017/31946, dated Nov. 13, 2018, 8 pages.
Barkmeier et al., "High inter-reviewer variability of spike detection on intracranial EEG addressed by an automated multi-channel algorithm," Clin Neurophysiol, Jun. 2012, 19 pages.
Cimbalnik et al., "The CS algorithm: A novel method for high frequency oscillation detection in EEG," Journal of Neuroscience Methods, 2018, 11 pages.
Office Action in European Appln. No. 17796757.7, dated Jul. 31, 2023, 7 pages.
Watterson et al., "Fractal Electronics as a Generic Interface to Neurons," The Fractal Geometry of the Brain, Aug. 2016, 1-13.
Abend et al., "Interobserver reproducibility of electroencephalogram interpretation in critically ill children," J. Clin. Neurophysiology, Feb. 2011, 28(1):15-19.
Adeli et al., "Analysis of EEG records in an epileptic patient using wavelet transform," J. Neurosci. Methods, Feb. 15, 2003, 123(1):69-87.
Alkan et al., "Automatic seizure detection in EEG using logistic regression and artificial neural network," J. Neurosci. Methods, Oct. 30, 2005, 148(2):167-176.
Asano et al., "Quantitative interictal subdural EEG analyses in children with neocortical epilepsy," Epilepsia, Mar. 2003, 44(3):425-434.
Axmacher et al., "Ripples in the medial temporal lobe are relevant for human memory consolidation," Brain, Jul. 2008, 131(Pt 7):1806-1817.
Bergey et al., "Long-term treatment with responsive brain stimulation in adults with refractory partial seizures," Neurology, Feb. 24, 2015, 84(8):810-817.
Birot et al., "Automatic detection of fast ripples," J. Neurosci. Methods, Mar. 15, 2013, 213(2):236-249.
Blanco et al., "Data mining neocortical high-frequency oscillations in epilepsy and controls," Brain, Oct. 2011, 134(Pt 10):2948-2959.
Blanco et al., "Unsupervised classification of high-frequency oscillations in human neocortical epilepsy and control patients," J. Neurophysiology, Nov. 2010, 104(5):2900-2912.
Bragin et al., "High-frequency oscillations in human brain," Hippocampus, Apr. 15, 1999, 9(2):137-142.
Bragin et al., "Interictal high-frequency oscillations (80-500 Hz) in the human epileptic brain: entorhinal cortex," Ann. Neurology, Oct. 2002, 52(4):407-415.
Brinkmann et al., "Large-scale electrophysiology: acquisition, compression, encryption, and storage of big data," J. Neurosci. Methods, May 30, 2009, 180(1):185-192.
Burnos et al., "Human intracranial high frequency oscillations (HFOs) detected by automatic time-frequency analysis," PLoS One, Apr. 10, 2014, 9(4):e94381, 12 pages.
Buzsáki et al., "High frequency oscillations in the intact brain," Prog. Neurobiology, Sep. 2012, 98(3):241-249.
Buzsáki et al., "High-frequency network oscillation in the hippocampus," Science, May 15, 1992, 256(5059):1025-1027.
Buzsáki, "Large-scale recording of neuronal ensembles," Nat. Neuroscience, May 2004, 7(5):446-451.
Carrie, "A hybrid computer technique for detecting sharp EEG transients," Electroencephalogr. Clin. Neurophysiology, Sep. 1972, 33(3):336-338.
Carrie, "Zero-cross EEG analysis: effects of noise," Int. J. Biomed. Computing, 1973, 4(2):97-103.
Chaibi et al., "Automated detection and classification of high frequency oscillations (HFOs) in human intracereberal EEG," Biomed. Signal Process. Control, 8(6), pp. 927-934.
Child et al., "Chronic subthreshold subdural cortical stimulation for the treatment of focal epilepsy originating from eloquent cortex," Epilepsia, Mar. 2014, 55(3):e18-e21.
Clarençon et al., "Real-time spike detection in EEG signals using the wavelet transform and a dedicated digital signal processor card," J. Neurosci. Methods, Dec. 1996, 70(1):5-14.
Cranstoun et al., "Time-frequency spectral estimation of multichannel EEG using the Auto-SLEX method," IEEE Trans. Biomed. Engineering, Sep. 2002, 49(9):988-996.
Delorme et al., "Enhanced detection of artifacts in EEG data using higher-order statistics and independent component analysis," Neuroimage, Feb. 15, 2007, 34(4):1443-1449.
Donoho, "An invitation to reproducible computational research," Biostatistics, Jul. 2010, 11(3):385-388.
Donovan, "Big data: teaching must evolve to keep up with advances," Nature, Sep. 25, 2008, 455(7212):461.
Dümpelmann et al., "Automatic 80-250Hz "ripple" high frequency oscillation detection in invasive subdural grid and strip recordings in epilepsy by a radial basis function neural network," Clin. Neurophysiology, Sep. 2012, 123(9):1721-1731.
Echauz et al., "Long-Term Validation of Detection Algorithms Suitable for an Implantable Device," Abstract 1.107, Presented at

(56) References Cited

OTHER PUBLICATIONS

Proceedings of the Annual Meeting of the American Epilepsy Society, Philadelphia, PA, USA, Nov. 30-Dec. 5, 2001, 2 pages.
Esteller et al., "Line Length: an efficient feature for seizure onset detection," Presented at Proceedings of the 23rd Annual International Conference of the IEEE Engineering in Medicine and Biology Society, Istanbul, Turkey, Oct. 25-28, 2001, 4 pages.
Gabor, "Seizure detection using a self-organizing neural network: validation and comparison with other detection strategies," Electroencephalogr. Clin. Neurophysiology, Jul. 1998, 107(1):27-32.
Gardner et al., "Human and automated detection of high-frequency oscillations in clinical intracranial EEG recordings," Clin. Neurophysiology, May 2007, 118(5):1134-1143.
Gardner et al., "One-Class Novelty Detection for Seizure Analysis from Intracranial Eeg," J. Mach. Learn. Research, Jun. 2006, 7:1025-1044.
Gardner, "A Novelty Detection Approach to Seizure Analysis from Intracranial EEG, in Electrical and Computer Engineering," Dissertation for the degree of Doctor of Philosophy in Electrical Engineering, Georgia Institute of Technology, Apr. 2004, 160 pages.
Ghosh-Dastidar et al., "Principal component analysis-enhanced cosine radial basis function neural network for robust epilepsy and seizure detection," IEEE Trans. Biomed. Engineering, Jan. 16, 2008, 55(2):512-518.
Gotman et al., "Automatic recognition and quantification of interictal epileptic activity in the human scalp EEG," Electroencephalogr. Clin. Neurophysiology, Nov. 1976, 41(5):513-529.
Gotman, "Automatic detection of seizures and spikes," J. Clin. Neurophysiology, Mar. 1999, 16(2):130-140.
Gotman, "Automatic recognition of interictal spikes," Electroencephalogr. Clin. Neurophysiol. Supplement, 1985, 37:93-114.
Gotman, "Automatic seizure detection: improvements and evaluation," Electroencephalogr. Clin. Neurophysiology, Oct. 1990, 76(4):317-324.
Gross et al., "Correlation of high-frequency oscillations with the sleep-wake cycle and cognitive activity in humans," Neuroscience, 1999, 94(4):1005-1018.
Hu et al., "Automatic identification and removal of scalp reference signal for intracranial EEGs based on independent component analysis," IEEE Trans. Biomed. Engineering, Sep. 2007, 54(9):1560-1572.
Jacobs et al., "High-frequency electroencephalographic oscillations correlate with outcome of epilepsy surgery," Ann. Neurology, Feb. 2010, 67(2):209-220.
Jadhav et al., "Awake Hippocampal Sharp-Wave Ripples Support Spatial Memory," Science, Jun. 15, 2012, 336(6087):1454-1458.
Jirsch et al., "High-frequency oscillations during human focal seizures," Brain, Jun. 2006, 129(Pt 6):1593-1608.
Khodagholy et al., "NeuroGrid: recording action potentials from the surface of the brain," Nat. Neuroscience, Dec. 22, 2014, 18(2):310-315.
Krendl et al., "Absolute spike frequency predicts surgical outcome in TLE with unilateral hippocampal atrophy," Neurology, Aug. 5, 2008, 71(6):413-418.
Kucewicz et al., "High frequency oscillations are associated with cognitive processing in human recognition memory," Brain, Aug. 2014, 137(Pt 8):2231-2244.
Lagerlund et al., "Spatial filtering of multichannel electroencephalographic recordings through principal component analysis by singular value decomposition," J. Clin. Neurophysiology, Jan. 1997, 14(1):73-82.
Lagerlund et al., "Use of principal component analysis in the frequency domain for mapping electroencephalographic activities: comparison with phase-encoded Fourier spectral analysis," Brain Topography, Dec. 2004, 17(2):73-84.
Lee, "Big data: open-source format needed to aid wiki collaboration," Nature, Sep. 25, 2008, 455(7212):461.
Likert, "A Technique for the Measurement of Attitudes," Arch. Psychology, 1932, 22(140):5-55.
Morrell, "Brain stimulation for epilepsy: can scheduled or responsive neurostimulation stop seizures?," Curr. Opin. Neurology, Apr. 2006, 19(2):164-168.
Osorio et al., "Performance reassessment of a real-time seizure-detection algorithm on long ECoG series," Epilepsia, Dec. 2002, 43(12):1522-1535.
Osorio et al., "Real-time automated detection and quantitative analysis of seizures and short-term prediction of clinical onset," Epilepsia, Jun. 1998, 39(6):615-627.
Qu et al., "A patient-specific algorithm for the detection of seizure onset in long-term EEG monitoring: possible use as a warning device," IEEE Trans. Biomed. Engineering, Feb. 1997, 44(2):115-122.
Qu et al., "A seizure warning system for long-term epilepsy monitoring," Neurology, Dec. 1995, 45(12):2250-2254.
Radhakrishnan et al., "Predictors of outcome of anterior temporal lobectomy for intractable epilepsy: a multivariate study," Neurology, Aug. 1998, 51(2):465-471.
Saab et al., "A system to detect the onset of epileptic seizures in scalp EEG," Clin. Neurophysiology, Feb. 2005, 116(2):427-442.
Srinivasan et al., "Approximate entropy-based epileptic EEG detection using artificial neural networks," IEEE Trans. Inf. Technol. Biomedicine, May 2007, 11(3):288-295.
Staba et al., "High-frequency oscillations recorded in human medial temporal lobe during sleep," Ann. Neurology, Jul. 2004, 56(1):108-115.
Staba et al., "Quantitative analysis of high-frequency oscillations (80-500 Hz) recorded in human epileptic hippocampus and entorhinal cortex," J. Neurophysiology, Oct. 2002, 88(4):1743-1752.
Stead et al., "Microseizures and the spatiotemporal scales of human partial epilepsy," Brain, Sep. 2010, 133(9):2789-2797.
Swets et al., "Better decisions through science," Sci. American, Oct. 2000, 283(4):82-87.
Urrestarazu et al., "Interictal high-frequency oscillations (100-500 Hz) in the intracerebral EEG of epileptic patients," Brain, Sep. 2007, 130(Pt 9):2354-2366.
Usui et al., "Digital low-pass differentiation for biological signal processing," IEEE Trans. Biomed. Engineering, Oct. 1982, 29(10):686-693.
Vanhatalo et al., "Full-band EEG (FbEEG): an emerging standard in electroencephalography," Clin. Neurophysiology, Jan. 2005, 116(1):1-8.
Velasco et al., "Neuromodulation of epileptic foci in patients with non-lesional refractory motor epilepsy," Int. J. Neural Systems, 2009, 19(3):139-147.
Webber et al., "An approach to seizure detection using an artificial neural network (ANN)," Electroencephalogr. Clin. Neurophysiology, Apr. 1996, 98(4):250-272.
Wilson et al., "Seizure detection: correlation of human experts," Clin. Neurophysiology, Nov. 2003, 114(11):2156-2164.
Wilson et al., "Seizure detection: evaluation of the Reveal algorithm," Clin. Neurophysiology, Oct. 2004, 115(10):2280-2291.
Wilson et al., "Spike detection: a review and comparison of algorithms," Clin. Neurophysiology, Dec. 2002, 113(12):1873-1881.
Worrell et al., "High-frequency oscillations and seizure generation in neocortical epilepsy," Brain, Jul. 2004, 127(Pt 7):1496-1506.
Worrell et al., "High-frequency oscillations in human temporal lobe: simultaneous microwire and clinical macroelectrode recordings," Brain, Apr. 2008, 131(Pt 4):928-937.
Yamamoto et al., "Low-frequency electric cortical stimulation decreases interictal and ictal activity in human epilepsy," Seizure, Oct. 2006, 15(7):520-527.
Zelmann et al., "A comparison between detectors of high frequency oscillations," Clin. Neurophysiology, January 20120, 123(1):106-116.
Zelmann et al., "Automatic detector of High Frequency Oscillations for human recordings with macroelectrodes," Presented at Proceedings of the 2010 Annual International Conference of the IEEE Engineering in Medicine and Biology, Buenos Aires, Argentina, Aug. 31-Sep. 4, 2010, 2329-2333.

(56) References Cited

OTHER PUBLICATIONS

Lundstrom et al., "Chronic Subthreshold Cortical Stimulation to Treat Focal Epilepsy," JAMA Neurol., Nov. 2016, 73(11):1370-1372.

* cited by examiner

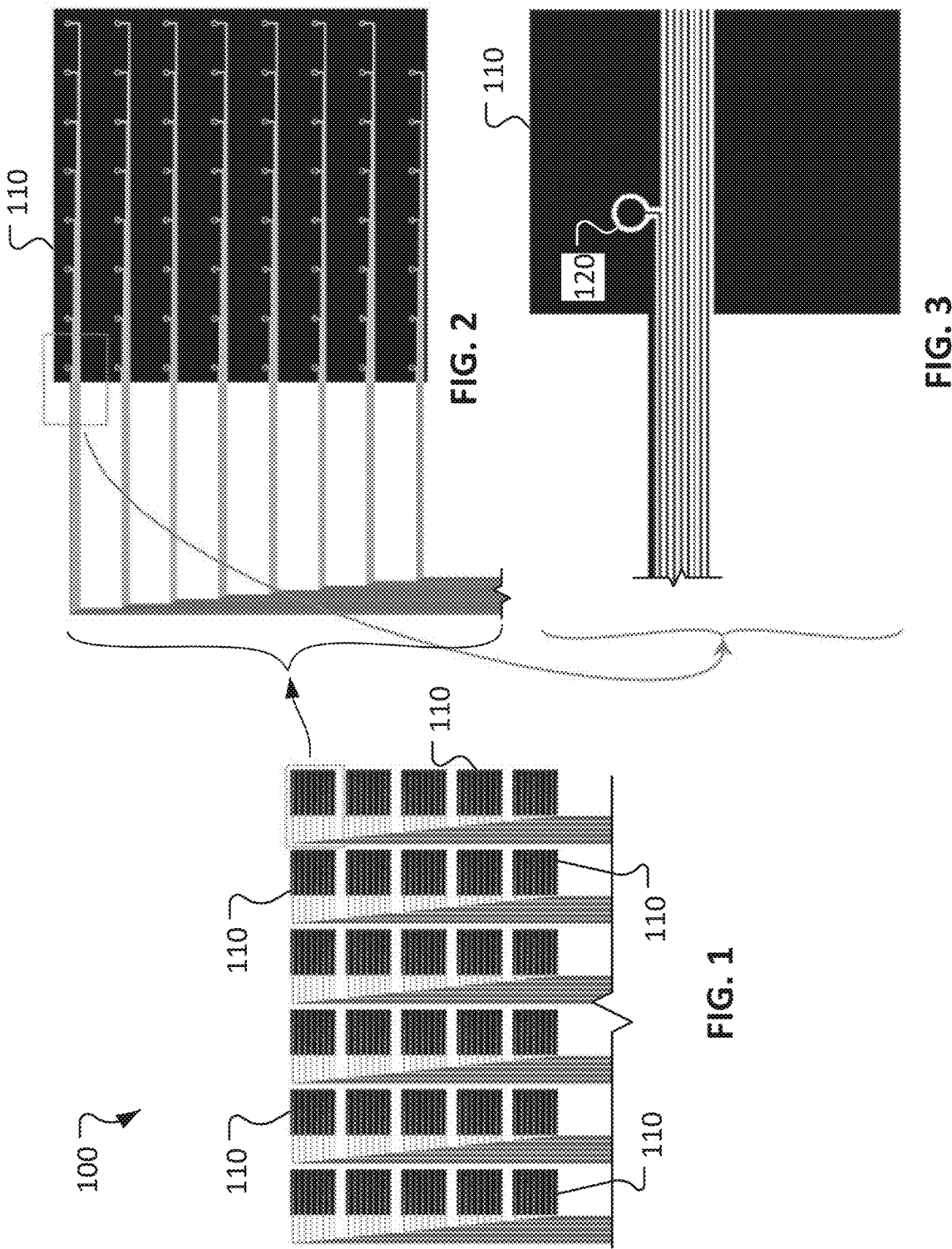

MULTISCALE BRAIN ELECTRODE DEVICES AND METHODS FOR USING THE MULTISCALE BRAIN ELECTRODES

CROSS-REFERENCE TO RELATED APPLICATIONS

This application is a continuation of U.S. patent application Ser. No. 16/098,335, filed Nov. 1, 2018, which is a National Stage application under 35 U.S.C. § 371 of International Application No. PCT/US2017/031946, having an International Filing Date of May 10, 2017, which claims the benefit of U.S. Provisional Application Ser. No. 62/334,843, filed May 11, 2016. The disclosure of the prior applications are applications are considered part of (and are incorporated by reference in) the disclosure of this application

STATEMENT AS TO FEDERALLY SPONSORED RESEARCH

This invention was made with government support under NS095495, NS092882, and NS078136 awarded by the National Institutes of Health. The government has certain rights in the invention.

BACKGROUND

1. Technical Field

This document relates to multiscale electrodes for spatiotemporal mapping, probing, and therapeutic modulation of the human brain.

2. Background Information

To effectively deliver electrical stimulation to probe and record the response of normal and pathological brain at the scales of single neurons, neuronal assemblies, local field potentials, and macroscopic EEG, the electrode surface area must be such that current can be safely delivered to the region and scale of interest and the brain response recorded at the scale of interest. Currently clinical practice protocols exist for stimulation of clinical macroelectrodes (about 1-10 $mm^2$ surface area; about 200-500Ω) including subdural grids, strips, and penetrating depth electrodes. There are research protocols for stimulation of single neurons and local populations using research microelectrodes (about 0.1-0.01 $mm^2$; impedance about 10 MΩ). It is of interest for brain mapping, similar to passive recording, to probe a brain with electrical stimulation and record response at a range of scales spanning from neurons, to macroscopic brain tissue underlying clinical macroelectrodes, to large-scale networks spanning different brain regions.

The networks of interest can be distributed anatomically and involving lobes (e.g., temporal and frontal lobes) over gyral crowns and within deep sulci of neocortex. Recording and probing cortical gyri with an optimal recording electrode is currently a significant challenge. Over two-thirds of the neocortex is not directly accessible, and within brain sulci. Thus, the challenges of effectively probing the multiscale spatiotemporal dynamics of brain activity include the following issues.

The inherent multiscale organization of brain (e.g., spatial scales of about 10 μm to about $10^5$ μm; and temporal scale of about DC to about 10,000 Hz). The local field potentials generated by the neuronal assemblies (neural networks) of interest span about DC to about 1,000 Hz. Integration of stimulation and recording electrodes to probe the relevant range of spatiotemporal scales has applications for probing and controlling brain activity. For large scale clinical stimulation protocols, macroelectrodes (e.g., about 1 $mm^2$ to about 10 $mm^2$) are used. To record activity on a microdomain and to deliver micro-stimulation to probe normal and pathological local neuronal assemblies, microelectrodes (e.g., about 10 μm to about 100 μm) are required. Delivery of subdural electrodes to the brain currently utilize a large craniotomy that is approximately the dimensions of the subdural grid, strips and smaller grids may be slipped under the dura, and penetrating depth electrodes can target deep structures (e.g. hippocampus, amygdala, thalamus etc.) or target cortex within the sulcal folds of the brain.

SUMMARY

This document provides multiscale electrodes for spatiotemporal mapping, probing, and therapeutic modulation of the human brain across the wide spatiotemporal range discussed above. The applications for such functional mapping and electrical stimulation modulation span, for example, neurological and psychiatric diseases, and brain rehabilitation.

Electrophysiological recordings can be used to probe and record the neuronal assemblies underlying normal and pathological brain activity. Because the electrical activity (e.g., single neuron activity, local field potential oscillations, and transients) of these neuronal assemblies span a wide range of spatiotemporal scales, the electrodes optimally will span similar spatial scales. Such scales range from single neurons to large-scale networks (e.g., about 10 μm to about $10^5$ μm) with temporal sampling (e.g., DC to about 10 kHz) to resolve single and multi-neuron extracellular spikes, local field potentials, including high frequency oscillations (>100 Hz) and ultraslow oscillations and DC shifts. There are a number of technical challenges with the acquisition and storage of this type of multiscale, in addition to the challenging spatially multiscale electrode interface required to probe and record these putative cellular assemblies. Below we describe multiscale electrodes that can be configured into strips, grids, and penetrating depth electrodes.

In one aspect, the disclosure is directed to a brain electrode device including one or more macroelectrodes; and a plurality of microelectrodes encompassed within each macroelectrode of the one or more macroelectrodes. Each microelectrode and each macroelectrode is electrically isolated.

Such a brain electrode device may optionally include one or more of the following features. The one or more macroelectrodes may include at least two macroelectrodes. The brain electrode may also include a plurality of additional electrodes that are larger than the microelectrodes and that are encompassed within each macroelectrode of the one or more macroelectrodes. The brain electrode device may be configured for permanent implantation in contact with a brain of a human patient. The one or more macroelectrodes may include at least ten macroelectrodes. The plurality of microelectrodes encompassed within each macroelectrode may include at least four microelectrodes. The plurality of microelectrodes encompassed within each macroelectrode may include at least 16 microelectrodes.

In another aspect, the disclosure is directed to a method of stimulating and mapping activity of a brain of a human patient. The method includes coupling a brain electrode device to the patient such that the brain electrode device can detect EEGs of the brain; providing an electrical stimulation to the brain from the one or more macroelectrodes; and after providing the electrical stimulation, detecting, using the plurality of microelectrodes, micro-EEGs from the brain. The brain electrode device includes one or more macroelectrodes; and a plurality of microelectrodes encompassed within each macroelectrode of the one or more macroelectrodes. Each microelectrode and each macroelectrode is electrically isolated.

Such a method of stimulating and mapping activity of a brain of a human patient may optionally include one or more of the following features. The method may also include recording EEGs from the brain using the one or more macroelectrodes. The method may also include determining, based on the micro-EEGs, the patient is having micro-seizures. The method may also include determining, based on the determining the patient is having micro-seizures, one or more seizure loci. The method may also include determining one or more loci based on determining the patient is having one of more of: (i) changes in pathological biomarkers recorded on the brain electrode device, (ii) micro epileptiform discharges, (iii) pathological high frequency oscillations, (iv) focal slow-wave oscillations, (v) micro DC-shifts, and (vi) micro-seizures.

In another aspect, the disclosure is directed to a brain electrode device for recording electrical and magnetic fields. The device includes one or more macroelectrodes and magnetometers; and a plurality of microelectrodes encompassed within each macroelectrode of the one or more macroelectrodes. Each microelectrode and each macroelectrode is electrically isolated.

In another aspect, the disclosure is directed to a system including one or more multiscale electrodes configured and operable for (i) actively probing, (ii) passively recording and (iii) measuring biomarkers including at least one of the group including interictal spikes, high frequency oscillations, focal slow oscillations, focal DC shifts, and micro-seizures of brain; and a computer processing system. The multiscale electrodes include one or more macroelectrodes; and a plurality of microelectrodes encompassed within each macroelectrode of the one or more macroelectrodes. Each microelectrode and each macroelectrode is electrically isolated. The computer processing system is configured and operable for: analyzing multi-scale electrophysiological data acquired from the one or more multiscale electrodes; and mapping epileptogenic brain using the multi-scale electrophysiological data acquired from the one or more multiscale electrodes.

Such a system may optionally include one or more of the following features. The biomarkers of the brain may be measured on micro-scales during an interictal state. In some cases, the interictal state is during intraoperative or during pharmacological interventions. The biomarkers of the brain may be measured on macro-scales during an interictal state. The interictal state may be during intraoperative or during pharmacological interventions. The biomarkers of the brain may be measured on micro-scales and on macro-scales during an interictal state. The interictal state may be during intraoperative or during pharmacological interventions.

Particular embodiments of the subject matter described in this document can be implemented to realize one or more of the following advantages. In some embodiments, by embedding isolated microelectrodes within macroelectrodes, current for stimulation can be provided via the macroelectrode(s) while responsive recordings of microscale EEGs can be captured by the microelectrodes. Such an arrangement can provide an advantageous means for capturing biomarkers (local field potential activity) that would otherwise go undetected, including microscale epileptiform spikes, sharpwaves, high frequency oscillations, focal slow oscillation, focal DC shifts, and micro-seizures. Moreover, in some such cases the macroscopic seizure loci responsible for generation of the patient habitual seizures can be mapped by quantifying and tracking the spontaneous and stimulation provoked microscale biomarker activity without having to wait for a seizure to happen naturally. Accordingly, time can be saved in some cases using the multiscale brain electrodes provided herein by incorporating the stimulation and mapping procedure intra-operative right at time before a treatment procedure. Further, using the multiscale brain electrodes provided herein, in some cases warnings of imminent seizure are ascertainable. In some such cases, treatment therapy can be provided to mitigate the seizure occurrence. In some such cases therapies, such as brain stimulation, can be adaptively delivered based on recording of interictal biomarker activity recorded from multi-scale electrodes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1 is a schematic diagram of an example multiscale electrode in accordance with some embodiments provided herein. The example multiscale electrode is a two-dimensional grid that can be used, for example, for cortical surface recording.

FIG. 2 is a schematic diagram of a macroelectrode portion of the multiscale electrode of FIG. 1.

FIG. 3 is a schematic diagram of a microelectrode portion of the macroelectrode of FIG. 2.

Like reference numbers represent corresponding parts throughout.

DETAILED DESCRIPTION

Figure 4:
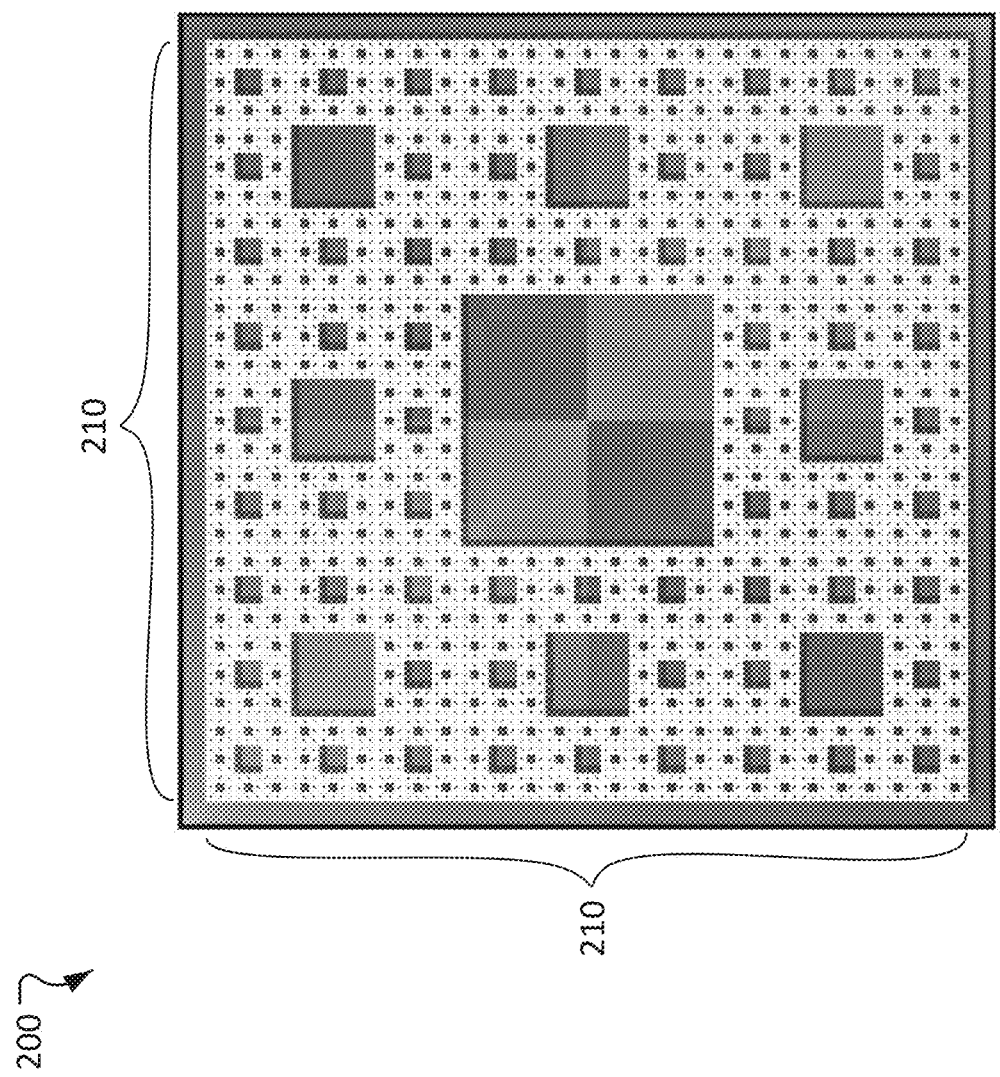
FIG. 4 is a schematic diagram of another example multiscale electrode in accordance with some embodiments provided herein.

This document provides multiscale electrodes for spatiotemporal mapping, probing, and therapeutic modulation of the human brain. The applications for such functional mapping and electrical stimulation modulation span, for example, neurological and psychiatric diseases, and brain rehabilitation.

With multiscale electrodes as provided herein, brain stimulation can be delivered at multiple spatial and temporal scales. In some embodiments, the multiscale electrodes provided herein have the ability to activate larger networks while examining localized constituents at finer spatial scales, from neurons, columns, to large-scale networks spanning lobar brain regions. In some embodiments provided herein, the multiscale electrodes are comprised as intercalated microwire arrays, which can span a range of different size scales, embedded into a macroelectrode.

Referring to FIGS. 1-3, an example multiscale brain electrode 100 includes a plurality of macroelectrodes 110 within which are encompassed a plurality of microelectrodes 120. That is, a plurality of microelectrodes 120 are encompassed within individual macroelectrodes 110. In some embodiments, each macroelectrode 110 of the plurality of macroelectrodes 110 encompasses a plurality of microelectrodes 120. In some embodiments, fewer than all macroelectrodes 110 of the plurality of macroelectrodes 110 encompass a plurality of microelectrodes 120.

In some examples, multiscale brain electrode 100 can be made on thin film (e.g., polyimide, etc.) using known manufacturing techniques including printing, etching, and the like. Such example materials and techniques are purely illustrative, and are non-limiting.

In some implementations, multiscale brain electrode 100 can be wrapped around a shaft designed for penetrating the brain to target deep structures. In some cases, a shaft with about a one millimeter diameter can be used.

FIG. 1 depicts the entire electrode assembly of example multiscale brain electrode 100. FIG. 2 depicts just one macroelectrode 110 (i.e., a portion of multiscale brain electrode 100 as depicted in FIG. 1). FIG. 3 depicts just one microelectrode 120 (i.e., a portion of macroelectrode 110 as depicted in FIG. 2).

Macroelectrodes 110 and microelectrodes 120 are electrically isolated from each other. Moreover, the plurality of macroelectrodes 110 are electrically isolated from each other, and the plurality of microelectrodes 120 are electrically isolated from each other.

In the depicted embodiment, macroelectrodes 110 are arranged in a five-by-six rectangular array (i.e., example multiscale brain electrode 100 includes a total of 30 macroelectrodes 110). It should be understood that the depicted embodiment is non-limiting and that any and all other arrangements (i.e., non-rectangular arrangements) and numbers of macroelectrodes 110 are also envisioned in the scope of this disclosure.

In the depicted embodiment, 63 microelectrodes 120 are encompassed in macroelectrode 110 and arranged in a generally square array. It should be understood that the depicted embodiment is non-limiting and that any and all other arrangements (i.e., non-square arrangements) and numbers of microelectrodes 120 within macroelectrode 110 are also envisioned in the scope of this disclosure.

Multiscale brain electrode 100 facilitates capture of EEG at a variety of different scales. Accordingly, multiscale brain electrode 100 can be used to stimulate and/or map a variety of areas of a brain (e.g., at macro areas and micro areas of the brain).

Microelectrodes 120 can collect micro-EEGs. Accordingly, multiscale brain electrode 100 can be useful for detecting micro-seizures and for identifying the loci of such micro-seizures.

In addition, multiscale brain electrode 100 can be used for macro-level stimulation (using macroelectrodes 110) and microscale recording of response (using microelectrodes 120). A range of stimulation and recording electrode configurations can be realized. Moreover, in some cases high frequency oscillations (HFO) and interictal spikes can be detected using multiscale brain electrode 100.

In some cases, a low-level of stimulation (e.g., within a range of about 30 microamps to about 12 milliamps, or about 30 microamps to about 200 microamps, etc.) is delivered via macroelectrodes 110 and responses are captured/detected by microelectrodes 120. In some such cases seizure loci can be mapped without having to wait for a seizure to happen naturally.

In some implementations, multiscale brain electrode 100 can be used for seizure detection or detection of microscale pathological biomarker activity and, optionally, treatment can be delivered in response to the detection. In some such implementations, multiscale brain electrode 100 can be permanently implanted in a patient and multiscale brain electrode 100 can function in a record mode. In some cases, stimulation can be utilized. When EEGs (macro level and/or micro level) are indicative of a seizure or impending seizure, a therapy such as a drug, electrical stimulation, and the like can be delivered to the patient.

In another implementation, multiscale brain electrode 100 can be used for dynamic impedance testing to determine the epileptogenecity (the probability of seizure occurrence) and predict seizures. That is, brain impedance (macro level and/or micro level) can be detected using multiscale brain electrode 100, and the impedance (and/or changes in impedance) can be used in an algorithm to predict seizures, guide therapies such as drug delivery, or adjust the parameters (amplitude, frequency, waveform shape etc.) of electrical stimulation and the like.

Referring to FIG. 4, another example multiscale brain electrode 200 includes a plurality of differently sized electrodes based on a fractal algorithm. In the depicted embodiment, three or more different sizes of electrodes are included. This example embodiment further illustrates the variety of design possibilities for the multiscale brain electrodes provided herein. Any and all such design possibilities for the multiscale brain electrodes are within the scope of this disclosure.

In the depicted example, multiscale brain electrode 200 includes a macroelectrode 210 that encompasses a plurality of differently sized smaller electrodes. In some embodiments, more than a single macroelectrode 210 is included. A multi-layered construct can be used to create multiscale brain electrode 200.

The square and circular areas within macroelectrode 210 represent the plurality of differently sized smaller electrodes. In some embodiments, two different sizes of electrodes within macroelectrode 210 are included. In some embodiments, more than two different sizes of electrodes within macroelectrode 210 are included. For example, three, four, five, six, seven, eight, nine, ten, or more than ten different sizes of electrodes within macroelectrode 210 are included in some embodiments.

It should be understood that the concepts described herein can be extended to more complex designs including tri-scale, quad-scale, embedded electrode designs as well as fractal multiscale electrodes. A fractal electrode design provides multiple recording scale factors embedded in a macro-stimulation electrode. The surface area of stimulation and recording electrodes is determined by the number of iterations of the algorithm generating the fractal structure. In some embodiments, the stimulation electrode is macroelectrode 210. Alternatively, the stimulation electrode(s) could be one or more of the types of smaller electrodes encompassed within macroelectrode 210. In some such embodiments, a limitation on stimulation current such that the charge density remains less than about 20 $uC/cm^2$ can be used, as currently accepted in human clinical practice. The contacts to the individual recording electrodes can be located on the backside, or second layer if needed to increase the range of scales probed. This could be combined with compressed sampling approach for temporal and spatial sampling density.

In addition, it should be understood that the fractal multiscale electrode design geometric configurations provided herein can be optimized for recording and localizing sulcal sources. The sulcal generator creates a tangential dipole that is not well localized with discrete array of subdural electrodes resting on cortical crowns. These sulcal sources can be best detected with concentric ring electrodes that can detect the LFP created by the sulcal (tangential dipole) generator, or thin film electrodes that are slipped into the sulcus under visualization. Such embodiments are within the scope of this disclosure.

It should be understood that this disclosure provides multiscale electrode designs (from bi-scale to multifractal scales spanning arbitrary resolutions) for passive recording and active probing of neural tissue. The designs overcome the fundamental limitation of simultaneous stimulation and recording across multiple spatial scales of interest. The designs make possible simultaneous stimulation of functional areas (requiring larger surface area) and recording responses across multiple spatial scales. The high resolution electrodes are embedded in the larger scale electrodes.

Designs are provided herein for stimulation and recording across the range of relevant spatial scales (e.g., about 10 μm to about $10^4$ μm, without limitation) and frequencies (e.g., DC to about 10,000 Hz, without limitation) of cortex for mapping normal brain function, and identifying the neurons, neuronal assemblies, and networks involved in neurological and psychiatric disease. These applications include, but are not limited to: epilepsy, central pain, movement disorders, brain machine interface devices, neurodegenerative disorders, and brain tumor mapping.

This disclosure also provides methods to identify generators within cortical sulci are claimed using optimal designed electrodes, patient specific models of cortex from patient's MRI, and bioelectric inverse solution. Similar electrodes using arrays of millimeter scale magnetometer arrays are included in scope. Sulcal generators are localized with subdural electrodes arrays utilizing an optimal configuration for detecting tangential dipoles created by generators within the sulcal walls, based on multi-scale concentric circular (annular arrays) electrode arrays and/or magnetometer arrays. In addition, such designs can provide the ability to dynamically reconfigure the recording montage to identify montage with large independent signal components (e.g., Laplacian montage to identify focal radial source). Conversely, tangential source can be optimized. Scanning over an array of radially-oriented electrodes to identify the orientation of maximal field is also envisioned.

Dynamic montage sampling is provided herein. For example, electronics can be used to dynamically sample electrode arrays in order to localize normal and pathological patterns of activity or maximal fields. This can also include sampling from, and intelligence to, localize and record from vastly more electrodes than is currently possible because of electronics limitations.

Actively scanning over different montages to sample from a large number of electrodes using dynamic re-montaging is also within the scope of this disclosure. This makes it possible to sample wide spatial areas. Application of compressed sampling applied to high spatial resolution and multi-scale electrode grids to optimize the challenge of data and spatial resolution and localization of cortical generators can be utilized.

Penetrating depth electrodes utilizing the multi-scale electrode arrays are included in the scope of this disclosure. Such penetrating depth electrodes utilizing the multi-scale electrode arrays can be used to investigate deep brain structures. Some examples include hippocampus and thalamus, but the application is not limited to these structures.

Some embodiments of the multi-scale electrodes provided herein can be used for an Epilepsy NeuroRestoration technique. Epilepsy NeuroRestoration is an approach to normalize pathological epileptogenic brain using continuous electrical brain stimulation based on real-time biomarker tracking. The region of brain that generates spontaneous, unprovoked seizures is mapped and an optimal stimulation paradigm determined during the Phase II monitoring for epilepsy surgery. The approach, as detailed below, is used to dynamically tune brain stimulation to reduce novel multi-scale biomarkers that are surrogates for spontaneous seizures, and can be used to dynamically reduce the epileptogenicity of epileptic brain. The approach can be used during prolonged intracranial EEG monitoring during the phase II evaluation, and then subsequently embedded into a device that dynamically tracks multiscale biomarkers.

Multiscale recording and stimulation electrodes and systems, as provided herein, can be used for feedback-guided stimulation to control brain activity. In some embodiments, such a device or system is capable of the following:

1.) Identifying regions of epileptic brain from multiscale recording of spontaneous epileptiform biomarkers and stimulus-induced epileptiform biomarkers;
2.) Identifying periods of increased probability of seizures, temporal profile of epileptogenicity, based on changes in multiscale recording of stimulus-induced epileptiform activity biomarkers; and
3.) Restoring pathological brain regions and preventing seizures by tailored electrical stimulation delivered in response to microdomain and macrodomain biomarker activity that is tracked in real-time to guide therapeutic stimulation to restore normal brain state.

Multiscale electrophysiology recording and stimulation approaches can use multiscale electrode arrays (e.g., as described above) of various suitably-sized micro and macroelectrodes for recording and electrical stimulation across the range of spatiotemporal scales involved in seizure generation. For example, the microelectrode (e.g., 10-100 micron electrodes with 100-1000 micron spacing) arrays can be used to continuously monitor the iEEG activity and epileptiform biomarkers of sub-millimeter regions or islands (e.g., independent microdomains –100-1000 micron diameter) throughout the epileptogenic zone of brain tissue. Such microelectrodes can be combined with macroelectrodes (e.g., 1-5 mm diameter with 5-10 mm spacing) that provide large spatial scale information and can deliver electrical stimulation. The macroelectrode electrical stimulation allows direct modulation of the epileptic brain and neuronal populations comprising microdomain activity, which is simultaneously monitored by microelectrode recordings. Macroelectrode Stimulation can be Used to/for the Following:

1.) Control microdomain and macroscale epileptiform activity, including but not limited to suppressing microseizures, and micro & macroscale pathological high frequency local field oscillation and interictal epileptiform spike rates by delivering stimulation that is actively tuned via a feedback control system to reduce rates of biomarker events. The stimulation can also include direct counter electrical field operating on slow time scales (about 0.001 Hz) to fast (about 1000 Hz) time scales that exactly cancels the ongoing local field activity recorded from multiscale micro & macro iEEG. Microelectrode (scale of neurons & cortical column 20-1000 um) electrode recordings are used to continuously monitor microdomain iEEG, multiunit, and single neuronal unit activity and used to guide the feedback control signal from the macroelectrodes.

2.) Modulation of epileptic microdomains and measurement of the stimulus-induced epileptiform activity of these regions to identify epileptic brain and states of increased seizure probability (i.e., the pre-ictal period).

3.) The generation of focal seizures results from the progressive network coalescence of microseizure islands. The microseizures are precursor events to the onset of macroscale seizures, and cannot be detected by macroelectrodes or limited microwire recordings of the type used in the prior art and described above. Identified microseizures can be used alone or in combination with monitored high-frequency epileptiform oscillations (HFEO), DC fluctuations and/or other biomarkers to identify periods where the brain is in a state of high seizure probability, and guide stimulation or other therapeutic interventions. Additionally, stimulation of regions of epileptic brain and simultaneous microdomain recordings can be used to identify regions of epileptic brain, probe networks, and to identify periods of increased probability of seizure occurrence.

In some cases, the following NeuroRestoration protocol (over about 1-3 days) can be used: 1) Initiate chronic stimulation & optimize parameters for suppression of biomarkers; 2) Evaluate closed loop modulation of biomarkers if possible within time constraint; 3) Implant chronic stimulating electrodes over the seizure focus and a programmable stimulator device capable of stimulation and sensing; 4) Restore medication dosages to pre-operative levels; 5) Set stimulation parameters to optimal settings found during trial period; and 6) Intiate electronic seizure diarying on the programmable stimulator device capable of stimulation and sensing.

In some cases, the following Chronic Stimulation NeuroRestoration protocol can be used: 1) Chronic stimulation with optimize parameters for suppression of biomarkers; 2) Closed loop modulation of biomarkers stimulating electrodes over the seizure focus and the stimulator; and 3) Intiate electronic seizure diarying on the programmable stimulator device capable of stimulation and sensing.

The following working examples provide illustrative applications of the multiscale brain electrodes described above, and provide further innovative concepts that are also within the scope of this disclosure.

Working Example #1 (Chronic Subthreshold Cortical Stimulation to Treat Focal Epilepsy)

INTRODUCTION: Approximately one to three in 1,000 people have focal drug resistant epilepsy (DRE). Epilepsy surgery is the most effective treatment but may not be feasible when seizures originate from critical cortical areas, i.e. eloquent cortex. Despite evidence for efficacy, current approaches to focal brain stimulation rarely yield seizure free outcomes. In this working example, 13 patients were treated with continuous subthreshold electrical cortical stimulation, which led to suppression of interictal epileptiform discharges (IEDs) and improvement in clinical seizures.

Figure 5:
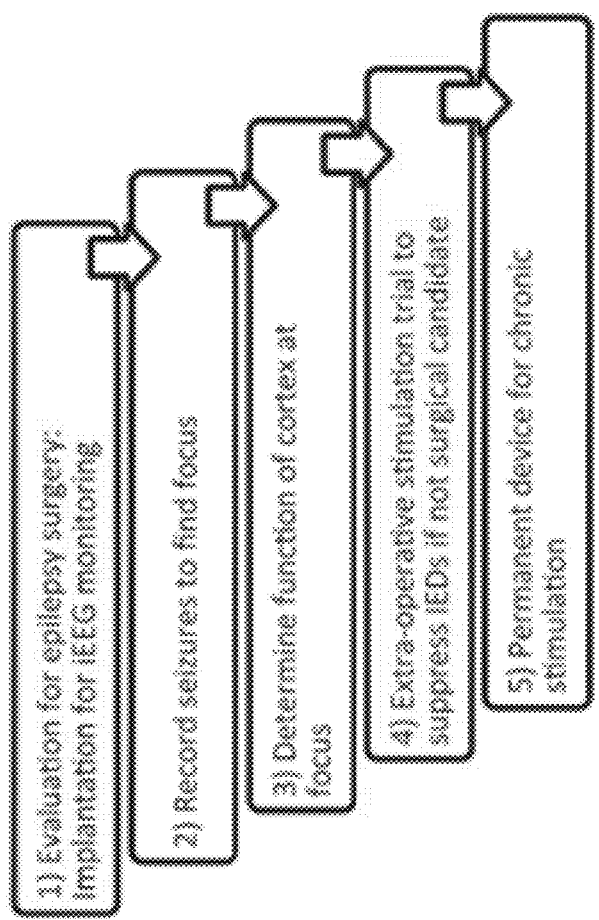
FIG. 5 is a flowchart of an example method of using the multiscale electrodes in accordance with some embodiments provided herein.

METHODS: Thirteen patients with focal DRE were deemed unsuitable for resective surgery following intracranial electroencephalography (iEEG) monitoring with surgically implanted subdural grid and depth electrodes (see FIG. 5 showing steps of patient evaluation and treatment). Pre-stimulation monitoring was typically several days, as clinically determined to accurately estimate the seizure focus. If not a surgical candidate, they were offered a therapeutic trial of continuous cortical stimulation (biphasic, 2-100 Hz, pulse width 90-450 µs, amplitude 1-6 V in voltage mode) via adjacent strip and occasional depth electrodes in the region of seizure onset. Permanent stimulation hardware (16-contact Medtronic PrimeAdvanced Neurostimulator with Medtronic 6 $mm^2$ platinum-iridium 2×8 surgical leads or DBS electrodes 3387, 3389 or 3391) was implanted when iEEG electrodes were explanted.

Data were analyzed retrospectively. IED rates were quantified for patients undergoing stimulation at 2 Hz who had 24 hours of pre- and post-stimulation iEEG data available for analysis (n=6). Patients stimulated at ≥2 Hz (n=7) were excluded from IED rate analysis due to artifact. Six 15-minute blocks from a 24-hour period of 500-Hz sampled data were analyzed before and during stimulation. IEDs were automatically detected using a previously validated method in five electrodes per patient (electrode with the highest IED rate and four background electrodes). To account for stimulation artifact, spike time differences of [2, 1, 0.5] Hz+/−2 ms were removed for pre- and post-stimulation data. Results from IED rates calculated via manual detection for three patients using 1 hour of data were similar. Assessment of epilepsy severity and life satisfaction (scale 1-10) as well as frequency of disabling seizures was based on retrospective patient report.

RESULTS: Ten (77%) of the 13 patients reported improvement for both epilepsy severity and life satisfaction following chronic stimulation. Mean count of disabling seizures decreased by 78% (50-100%), mean epilepsy severity decreased from 7±1.9 to 2.5±2.9 (p=0.002), and mean life satisfaction improved from 4.7±2.4 to 7.4±1.4 (p=0.004). Patients tolerated permanent implantation without serious side effects. IED rates decreased significantly for all analyzed patients, with three patients achieving near complete cessation of IEDs. The reduction in IED rate occurred within minutes of initiating stimulation. The mean IED rate decreased from 0.61 to 0.08 IED/s (p=0.002).

These results suggest clinical benefit and quantitative reduction in IED rate following subthreshold cortical stimulation. The majority of patients experienced >50% reduction in seizures, and the reduction in IED rate with cortical stimulation was pronounced. The immediate reduction in IED rate at the time of stimulation in conjunction with clinical improvement suggests that TED rate correlates with seizure probability. Clinically, IED rate can be a biomarker for treatment efficacy.

Working Example #2 (Multimodal Brain Mapping and Tracking)

INTRODUCTION: Multimodal imaging of brain integrates complementary neurophysiological signals from multiple modalities at multiple scales to make classifications of tissue epileptogenicity. The modalities include, but are not limited to, SPECT, PET, MRI structure, and wide bandwidth multi-scale Electrophysiology. SPECT, PET, and multiscale continuous (days to week, from hundreds of channels, sampled at 32 kHz) local field potential (LFP) intracranial recordings from human subjects have been acquired using some embodiments of the multiscale brain electrodes described above.

This example in conjunction with the other disclosure provided herein encompasses at least the following innovative concepts:

1) A database of normal SPECT, PET, and LFP data from specific brain structures (Frontal, Temporal, sub-Temporal, medial temporal Parietal, Occipital) and specific functional regions (motor, sensory, language).
2) A software platform integrating large-scale database, viewer, and analysis tools for expert-review (manual), automated labeling of events, performance statistics, and mapping and tracking of anomalies in multiscale electrophysiology recordings. Examples include labeling: microseizures, microDC, DC changes, HFO, LFP spectral anomalies, epileptiform spikes in large-scale records. This tool allows for development and detector tuning against markings in a gold standard database.
3) Automated functional brain tissue labeling (epileptic, normal) and identifying the region generating spontaneous seizures (putative epileptogenic zone) based on spatial and temporal statistical maps of electrophysiology annomalies (e.g. microseizures, microDC, HFO, LFP spectral annomalies, epileptiform spikes) using normalitive data as statistical control.
4) Automated seizure forecasting based on statistical temporal profiling of microseizures, microDC, HFO, LFP spectral annomalies, epileptiform spikes using Non-EZ and normal control distributions to identify anomalies.
5) Interactive-time Statistical Mapping of LFP activity (e.g., psd, correlations, phase synchrony) using anatomical normalitive data for anomaly and epileptic event detection (Electrophysiological Statisitical Mapping of Ultraslow, Delta, Theta, Alpha. Beta, Gamma, HFO, and Microseizures, MicroDC shifts, spikes, subclinical seizures). In some cases, this includes: a) from above selection of outlier (annomally events for each feature, electrode specific, anatomic location specific), b) co-register onto MRI and functional studies (fMRI, PET, SPECT), and c) normal function mapping (Motor cortex, Language . . . application of Hilbert Tform).
6) Statistical temporal profiling of event anomaly occurrence for localization. In some cases, this includes: a) Statistical comparison to Database of normal controls and non-SOZ, and b) Outliers in inter-event intervals, statistical distribution of intervals, change in distribution (Gaussian→long-tail etc.).
7) Temporal profiling of epileptiform events (spikes & HFO) and the association of population epileptiform spikes and phase. Represents coincident detection of LFP phase (e.g. Ultraslow, or slow LFP oscillation phase and epileptiform spikes). Regions of brain ultimately generating seizures generate epileptiform transients with unit temporal distributions allowing the spatial and temporal localization and prediction of seizures. In some cases, this includes: a) Identify events, b) Hilbert Transform for (band specific) LFP phase, and c) Event timing and phase relation.
8) Endogenous Pinging: Peri-event analysis of spontaneous epileptiform spikes. Perievent statistics of the LFP oscillations (Ultraslow, Delta, Theta, Alpha, Beta, Gamma. HFO activity (DC-5000 Hz)) and discrete events Microseizures, MicroDC shifts, spikes, and subclinical seizures triggered by endogenous spontaneous epileptiform spikes will be mapped. The mapping can be used as measure of epileptogenicity of tissue and susceptibility to seizures (normal brain, epileptogenic zone, and pre-seizure period).
9) Exogenous Pinging: The region of interest is directly stimulated using electrical stimulation to intracranial macroelectrodes or with DC stimulation at scalp or transcranial magnetic stimulation. The stimulus response is analyzed for tissue spectal impedance, LFP oscillations (Ultraslow, Delta, Theta, Alpha, Beta, Gamma, HFO activity (DC-5000 Hz)) and discrete events Microseizures, MicroDC shifts, spikes, and subclinical seizures triggered by exogenous stimulation.

Detection of submillimeter and macro domain LFP anomalies (e.g., microseizures, microDC, band PSD) can be achieved, for example, using the following procedural steps:

1) Segmentation of the Data
   Time window (~10-100× event of interest),
   Behavioral state labeling,
   Electrode anatomic location.
2) Scrubbing Data and Anomalies
   Line noise removal algorithm,
   Remove artifact segments (e.g. using a clustering approach),
   Large amplitude events (e.g., based on normalitive and epilepsy database distributions),
   Coincident events across multiple channels,
   Potential false artifact detection are seizures.
3) Calculate Features of Interest
   Univariate: Line-length (LL), Line-length plus duration (LL+), band-pass LL, band integrated PSD, band energy, focal DC-signal change (100 ms change),
   Hilbert transform for amplitude and phase,
   HFO detection,
   Bivariate: correlation, phase synchrony,
   Multivariate: Correlation,
   Features to distinguish pathological from normal oscillations (delta, beta, gamma, HFO). Will depend on sleep/state, drug, lobe and stimulation.
4) Identify statistical outliers compared to database of normal controls & non-seizure generating epilepsy patients. This can include anatomic specific control data, such as frontal, temporal neocortex, hippocampus, motor or sensory cortex (may further select non-parametric outliers CDF ~10% from epilepsy group).

A classifier may be used to label each analysis window of EEG as "event" or "non-event." In effect the classifier maps regions of feature space to labels. The degree of difficulty in learning this map is directly related to the appropriateness of the selected features, classifier and the training method employed. Examples of classification approaches applied to EEG event detection can include: 1.) Simple thresholding, 2.) Artificial neural networks, 3.) Support vector machines, 4.) Linear Discriminant Analysis, 5.) kNN Classifier, 6.) Expert rules, and 7.) Decision trees.

Using the devices, systems, and techniques described herein, the following innovative aspects can be performed/attained:

1) Detection of Neurophysiological Anomalies with multimodalities at multiple scales.
2) Spatiotemporal Mapping & Classification of Brain with multifeatures: a) wide bandwidth (DC-10 kHz), multiscale (10 um-10 cm) local field potential anomalies, b) Endogenous (interictal spikes) and Exogenous (electrical & magnetic stimulation) events and associated brain response. The active stimulation to trigger response, including tissue impedance measurement, for characterizing tissue physiology & pathology, c) Interictal & Ictal SPECT imaging, and d) Interictal PET.
3) Mapping epileptogenicity of brain (predilection for seizures) using above features in populations of normals and epilepsy patients within a machine learning paradigm.
4) Tracking probability of seizure occurrence.
5) Detection of microseizures, MicroDC shifts, High frequency oscillations (HFO) and LFP anomalies.
6) Detection & tracking of tissue spectral impedance.
7) Statistical mapping of LFP activity (psd, correlations, phase synchrony) using anatomical data from normal controls and anomaly (epileptic event) detection.
8) Statisitical Mapping of Electrophysiological Ultraslow, Delta, Theta, Alpha, Beta, Gamma, HFO activity (DC-5000 Hz), and mapping of discrete events Microseizures, MicroDC shifts, spikes, and subclinical seizures.
9) Statistical spatial and temporal distribution of electrophysiology anomalies compared to normal controls for localization of epileptic brain.
10) Hilbert Transform method for large-scale data.

Working Example #3 (Microseizure Detection and HFO Detection)

INTRODUCTION: This example includes methods for: 1) labeling microdomain epileptiform events called microseizures and HFO in large-scale EEG records, and 2) automated labeling brain tissue as epileptic and identifying the ictal onset zone (IOZ), i.e the brain regions generating spontaneous seizures, based on spatial maps of microseizure and HFO density.

High frequency oscillations (HFOs) are emerging as a promising biomarker of epileptogenic tissue. HFOs are spontaneous EEG transients with frequencies traditionally considered to range from 60 to 600 Hz with $4<=$cycles$<50$ that stand out from the background as discrete electrographic events. HFOs are usually divided into subgroups of high $\gamma$ (60-80 Hz), ripple (80-250) and fast ripple (250-600) bands (Bragin et al. 1999).

Video-EEG (v-EEG) monitoring has long been a cornerstone in the evaluation of patients with seizure disorders. Generally, the primary goal of long-term v-EEG is to record the patient's habitual seizures. However, even when seizures are not captured, the long-term interictal recording can be useful by recording interictal epileptiform activity. In particular, microdomain epileptiform transients called microseizures that are biomarkers of epileptic brain and the process of seizure generation have been identified by the inventors. These interictal multiscale recordings using hybrid electrodes containing microwires and clinical macroelectrodes show microseizures and HFO that are markedly increased in epileptic brain.

Recent advances in neurophysiologic data acquisition systems now enable recording over the physiological range of human brain activity [15-18]. Wide bandwidth EEG recordings (0.01-1000 Hz) show that interictal high-frequency oscillations are signatures of epileptic brain, and may have greater specificity than interictal spikes for the region of brain that must resected for seizure freedom. However, high-frequency oscillations are relatively short duration events (50-250 ms) that are difficult to visualize with standard clinical EEG viewing parameters. The development of automated HFO detectors is an area of active research. Recently high-frequency epileptiform transients, fast ripples and pathological gamma and ripple oscillations, have been described in iEEG recordings as specific interictal biomarkers of epileptic brain.

The development of multiscale EEG recording indicates that the entire EEG record, not only seizures, contains useful diagnostic information. However, identifying these epileptiform transients in continuous multi-day v-EEG recordings presents a practical challenge for manual visual review. In fact, even electrographic and subtle clinical seizures on the macroelectrodes are easily missed in long-term recordings that rely on expert visual review. Therefore, mining large EEG data sets to obtain quantitative information for ictal and interictal electrographic events is clinically relevant.

The inventors have recently demonstrated that HFO and microseizures are specific biomarkers of epileptic brain and the IOZ. The classification of brain into IOZ and non-IOZ can be performed after classification of microseizure events from continuous iEEG and mapping their spatial distribution. Regions of significantly increased microseizure and HFO density compared to normal baseline brain (obtained from controls) is epileptic, and capable of generating seizures. Similarly, the risk of impending seizure can be quantified by tracking the temporal density of HFO and microseizure events.

Time periods associated with relative increased, compared to previously recorded interictal recordings from same patient, are identified as increased risk of seizure occurrence. Most importantly, and of critical relevance to the current disclosure, the classification of brain and risk of seizures does not require high specificity detection of HFO or microseizures. The use of hypersensitive detection can be used to collapse the iEEG into a spatiotemporal sequence of event detections. While the sequence of event detections (microseizures and HFO) will contain false positives, the temporal distribution of the false positives should be randomly distributed temporally. It is only the channels (electrodes) exhibiting detections that significantly depart from such random distributions that will represent pathophysiological microseizure events.

To facilitate viewing and labeling iEEG, the inventors developed a custom iEEG viewing tool (multiscale iEEG View) that allows the reviewer to see candidate events, labeled by automated detection, as highlighted segments on the viewer. To create "gold standard" datasets the candidate events are then rejected or accepted using a mouse cursor to validate each of the labeled events. Candidate seizures on clinical macro and microelectrodes were identified with an automated detector using signal line-length as a feature and thresholded for hypersensitive detection. In addition, all patient events, nursing events, and clinical documented events were labeled for visual review of iEEG.

Candidate seizure events are subjected to post-hoc, expert visual review to verify or reject detected events in order to create gold standard datasets for evaluation of fully automated detectors, and for manual classification of epileptic brain. Candidate seizure detections were viewed as a single channel recording and verified or rejected by reviewers blinded to all channel and clinical information. The visual verification of a seizure discharge was based on the electrographical features of seizures that include: (i) Paroxysmal change in the background iEEG activity with a characteristic seizure onset pattern (Periodic spiking, Sentinel spike, Slow wave, Background attenuation followed by temporal evolution with distinct oscillation), (ii) Temporal and spectral evolution of the seizure discharge, (iii) Spatial evolution of the seizure discharge (not required, but commonly seen-note microseizures and micro-periodic discharges are isolated to single electrode and did not typically show spatial evolution), (iv) Discrete termination of seizure discharge, and (v) Post-ictal slowing, suppression of background, periodic spiking (not required, but commonly seen).

Focal periodic, or quasi-periodic epileptiform discharges were also frequently recorded from isolated clinical macro- and research microelectrodes. Even when present on clinical macroelectrodes this electrographic pattern was not associated with clinical seizure activity, and therefore was not labeled as seizure when occurring on either macro- or microelectrode arrays. Here events were labeled as µPED when they occurred on isolated microelectrodes, and the label of µSZ was reserved for electrographical discharges that demonstrate temporal and spectral evolution commonly associated with clinical seizures recorded on macroelectrodes, e.g. paroxysmal burst of high frequency oscillation disrupting the ongoing background that monotonically evolves to lower frequency, and higher amplitude oscillation.

The clinical ictal onset zone (IOZ) was defined by the macroelectrodes with the earliest clear iEEG change at electrographic seizure onset. The time of the earliest iEEG change and the associated macroelectrode(s) were selected as the electrographic macroseizure onset time and seizure onset zone location, respectively. Seizure onset times and location were determined by independent visual identification of a clear electrographic seizure discharge in macroelectrodes recordings, then looking back in the record for the earliest definite iEEG change contiguously associated with the seizure.

The ability to investigate in-vivo human epileptogenic brain across a wide range of spatial and temporal scales has produced remarkably rich data. A significant finding is microdomain seizure-like events, on isolated microelectrodes but not detected on adjacent clinical macroelectrodes or microelectrodes. These seizure-like events, or microseizures (µsz), are clinically silent electrographic events, detectable on single microelectrodes only. Focal periodic spikes isolated to single microwires were also observed. Microseizures can have spectral features, morphology and durations similar to electrographic seizures detected on macroelectrodes. Microseizures and µPED are subclinical, self-limiting, electrographic events that mostly remain isolated to single microwires. Most often they do not show the characteristic spatial evolution of macroelectrode seizures, i.e. spreading to involve larger regions of brain.

Automated microseizure Detection. The line-length (LL) feature was demonstrated to be a robust feature for seizure detection. Here the inventors used a first generation microseizure detector with the LL feature and a non-parametric adaptive threshold combined with a duration threshold or 5 seconds. The ground-truth microseizure data set was generated independently by expert visual review of 3 hour records of 10 microwire electrodes (reviewer blinded to all channel and clinical information). The representative performance achievable with this first generation detectors was previously used for HFO, i.e. hyper-sensitive detection followed by expert visual review. The inventors used a hyper-sensitive detector to initially screen the data and reduce the amount to be manually reviewed. Expert visual review using a custom viewer was performed to reject the relatively large number of false-positive detections (80-90%) of detections. The visual review of continuous iEEG was performed while blinded to all clinical data, including channel identifiers. The review of the entire video-EEG records for 14 patients yielded 59 (average 4.2 seizures/patient, range 1-7 seizures) clinical symptomatic and 7 asymptomatic electrographic (iEEG seizure discharge without clinical symptoms) seizures from the 748 clinical macroelectrodes. No seizures were identified in the two patients with facial pain and no history of epilepsy or seizures, and 1552 (average 155 per patient) microseizures from the microwire electrodes that were not associated with clinical symptoms.

Materials and Methods for HFO Detections: Fifteen intracranial EEG (iEEG) recordings of patients who underwent implantation of electrodes for treatment of intractable focal epilepsy were used. Two hours of clinical data was visually checked for noise and care was taken to select data that were at least two hours apart from seizures. Also included were two rodent and two canine intracranial EEG recordings, similarly vetted.

The recordings were taken from either clinical macroelectrodes (~12 mm$^2$ surface area) or microelectrodes (40 µm diameter). The macroelectrodes were sampled at 5000 or 400 Hz. The microelectrodes were sampled at 32 kHz. The range of electrode sizes, sampling rates, and species was important to ensure consistent performance across a range of conditions. Efficient Poisson normalization was employed to address the variance stemming from these differences, as well as variance in impedance in otherwise similar recording conditions.

The CS algorithm consists of several steps including raw data filtration, calculation of feature traces, normalization, detection and a cascade of thresholds based on gold standard detections.

During the filtration stage the raw iEEG data is filtered in a series of overlapping, exponentially spaced frequency bands (Butterworth bandpass filter, 3 poles). The initial version of the algorithm consisted of 17 bands (Supplemental data). To determine the bands of interest the XX recordings were analyzed with these narrower exponentially spaced overlapping band spanning the range from 40 to 900 Hz. The analysis revealed distinct peaks which allowed for band reduction to 4 frequency bands, thus simplifying the algorithm and reducing processing time. Each frequency band is treated separately in the detection process.

Three feature traces are computed in the first step of the detection process:

1. An Amplitude trace, which represents the instantaneous amplitude characteristics of the bandpass filtered signal;
2. A Frequency Dominance trace, which measures the local dominance of the band frequency in the raw signal; and
3. The Product trace, which is the product of Amplitude & Frequency Dominance traces.

The amplitude trace of the bandpass filtered signal is calculated by finding its peaks and troughs (inflection points). Linear interpolation between absolute values of inflection points is performed to match the number of samples in the original signal. A sliding window of length equal to the minimum number of cycles in the given frequency band at its center frequency (geometric mean of high and low cut-off frequencies) is applied to the interpolated signal and each value is replaced by the maximum value in the window. Finally the trace is Poisson normalized.

The relationship between the bandpass filtered data and low passed filtered data is used to calculate the frequency dominance trace, where the cut-off frequency of the low-passed data equals the high cut-off frequency of the band-passed data. This metric measures the extent to which the local signal of the band-passed data is present in the raw data, and is exquisitely insensitive to Gibbs' phenomenon. Both signals are processed as follows; the signal is differentiated and values >1 are set to 1, values <−1 are set to −1.

Each of these traces is replaced by its cumulative sum and high-pass filtered with the cut-off frequency equal to the low cut-off frequency of the bandpass filter. These are referred to a Local Oscillation Traces (LOTs). A sliding window with the length of minimum number of event cycles at the band's center frequency is applied to the band-passed signal and root mean square is calculated (RMS), thus generating "signal". Similarly, the RMS is calculated on a second trace constructed by subtracting the band passed local oscillation trace from the high passed one, generating the "noise". The frequency dominance trace is calculated as the instantaneous (pointwise) "signal-to-noise" ratio. As with the amplitude trace, this signal is processed by a sliding window where each value is replaced by the window's local maximum and Poisson normalized.

The product combines the Amplitude and Frequency Dominance traces as the dot product of both traces where values <0 (which occur due to the Poisson normalization) are set to 0 before multiplication. Poisson normalization is also applied to the final product trace.

The putative HFOs are detected in the product trace as events exceeding an "edge" threshold (set to a value of 1). If the gap between two detections is shorter than the minimum number of cycles for detection (set to a value of 4), the two detections are fused into one. Subsequently, five measures are calculated for each detection and evaluated in a cascade of boundary thresholds.

The boundary thresholds are based on the events produced by the detector by applying only the edge threshold; by expert visual review this achieves 100% sensitivity. The events were scored in each frequency band separately by three expert reviewers. The cumulative distributions of each measure were fitted with a gamma function and the parameters of these cumulative distribution functions (CDF) were stored in the code for the detector. The absolute boundary thresholds for each measure are calculated from these CDF based on two user defined relative thresholds, explained below.

Three measures are represented by the feature traces: Amplitude, Frequency Dominance and Product. The fourth measure is the number of cycles in the detection in each frequency band, which is extracted from the inflection point arrays used to generate the Amplitude trace. The fifth measure is composed of the sum of CDF values for the four other measures. The detector applies two user defined relative thresholds, referred to here as the "AND" and the "OR" thresholds; both can vary between 0 and 1. The AND threshold is used to extract feature values from the Amplitude, Frequency Dominance, Product, and Cycle gamma curves. If the corresponding values of the candidate detection is less than any of the threshold values, the detection is rejected. This threshold ensures a minimum amplitude, frequency, dominance, product, and number of cycles for every candidate detection. The detections that are not rejected by the AND threshold are then subjected to the OR threshold. This threshold is captures the fact that expert reviewers tend to accept detections that stand out with respect to at least one feature, although which feature can vary. The OR threshold is calculated from a "Combination" score and corresponding gamma curve. The Combination score is the sum of the CDF values of the candidate detection extracted from the corresponding gamma curves. The OR threshold value is extracted from the corresponding Combination score gamma curve. If the candidate event combination score is less than the combination threshold, the event is rejected. Although the performance is similar varying either the AND or the OR thresholds, we have been generally set the AND threshold to 0.0 (default value), and varied the OR threshold (default 0.2).

Each accepted detection in each band is added to a conglomerate detection trace. Due to the overlapping nature of the bands, it is not uncommon for the same event to be detected in more than one band. Conglomerate detections are constructed from all detections that overlap in time and demarcated from the earliest onset to the latest offset. Conglomerate detections are subject to no subsequent thresholding. HFOs that evolve significantly in frequency are best temporally demarcated in the conglomerate detections.

To evaluate algorithmic performance a gold standard dataset was acquired by running the detector with both the AND and OR thresholds set to 0, achieving 100% sensitivity. The detections were visually reviewed by three independent experts. To reduce reviewer error, each candidate event was present to each reviewer 3 times, in random order. To be accepted, the reviewer was required to have accepted the event in 2 out of the 3 presentations. Each of the 3 reviewer's final scoring was then compared to produce the final gold standard data set. In this case unanimity of acceptance was required, rather than 2 of 3. This was to ensure that all gold standard events would likely be accepted by any expert reviewer.

Receiver operating characteristic (ROC) analysis was performed by varying OR threshold and area under the curve was calculated (AUC) for all detections in the gold standard pool. A true positive detection (TP) was considered an event accepted by both the algorithm at a given threshold and gold standard data set. Likewise, a true negative (TN) was considered a detection rejected by both the algorithm at a given threshold and the gold standard data set.

The true negative set in the ROC analysis described above is vastly underestimated, because at thresholds of 0, although 100% sensitive, the detector only selects a small fraction of the data for candidate events. Therefore a second ROC analysis was performed considering detection time only. The true positive rates (TPR) and false positive rates (FPR) were calculated as follows for each threshold:

Definitions

TT=total time of all the recordings scored
APT=total time of gold standard positive detections
TP=total time of true positive detections
FP=total time of false positive detections
For each threshold:
TPR=TP/APT
ANT=TT−APT
SPC (specificity)=ANT−FP
FPR=1−SPC In order to evaluate the temporal precision of the CS detector, artificially created HFO events were inserted into an intracranial EEG recording acquired from a contact located in the white matter (where HFOs are generally not detected). The signal was reviewed to ensure absence of any pathologic activity and physiological HFO. The detection was performed with the lowest threshold to detect all events. Inserted artificial HFOs were matched with detections and their onsets and offsets compared. The performance was compared with a line-length (LL) detector (Gardner et al. 2007). The CS algorithm had mean differences of −4.6+/−5.3 ms for the onsets and 4.9+/−5.9 ms for the offsets. The LL algorithm had mean differences of −41.7+/−14.3 ms for the onsets and 53.5+/−10.1 ms for the offsets.

As described above, the inventor have developed a novel HFO detection algorithm that is suitable for processing of big datasets while efficiently eliminating false positive detections produced by sharp transients and dealing with EEG non-stationarity. Experience of expert reviewers is accounted for by a cascade of boundary thresholds calculated from visually marked events.

The algorithm for HFO detection in intracranial EEG recordings acquired data from both micro and macro electrodes. Non-stationarity of EEG signal is compensated by normalization of statistical windows and expert clinical experience is represented by a series of boundary thresholds for HFO features. Temporal localization of HFO onset and offset exceeds that of the line-length benchmark detector. Detection results do not focus only on HFO counts but provide information about HFO onset, offset, frequency, amplitude, and frequency distribution of the detections. The algorithm shows satisfactory unsupervised detection performance and speed to be used in a clinical setting.

Working Example #4 (Mapping, Tracking, Modulating Epileptic Tissue)

INTRODUCTION: The surgical treatment of refractory partial epilepsy is based on the concept that seizures begin in a discrete region of brain, the seizure onset zone (SOZ), and then propagate to a critical volume of adjacent susceptible tissue, the epileptogenic zone (EZ). To obtain seizure freedom, the SOZ and the surrounding EZ must be resected. Unfortunately, the EZ does not currently have an apriori electrophysiological definition, and is only a concept acknowledging that resection of the SOZ does not always lead to seizure freedom. In some patients a focal lesion can be identified on MRI, e.g. tumor, or a vascular malformation. If the EEG can demonstrate that the SOZ co-localizes with the MRI lesion, then complete resection of the lesion can produce a cure. The rate of seizure free outcomes in these selected patients can approach 80-90%, demonstrating the potential efficacy of epilepsy surgery. However, many patients do not have an MRI lesion, or the lesion extends into functionally eloquent brain, e.g. brain regions supporting language, that cannot be removed without causing a significant neurological deficit. Unfortunately, these patients make up 20-30% of pre-surgical evaluations at major epilepsy centers. For patients with normal MRI scans only 30-50% of those finally deemed surgical candidates will achieve seizure freedom, demonstrating the current limitation of epilepsy surgery.

One embodiment of the invention is a multiscale recording and stimulation system or device capable of: 1.) identifying regions of epileptic brain from multiscale recording of spontaneous epileptiform activity (interictal biomarkers) and stimulus-induced epileptiform biomarker activity, 2.) identifying periods of increased probability of seizures from multiscale recordings obtained with multiscale electrodes from stimulus-induced epileptiform activity, 3.) preventing seizures by tailored electrical stimulation delivered in response to microdomain and macrodomain epileptiform biomarker activity. Multiscale electrophysiology recording and stimulation approach use novel arrays of variable size micro and macroelectrodes that span multiple spatial scales, including but not limited to bi-scale and fractal scale electrodes, for recording and electrical stimulation across the range of spatiotemporal scales involved in seizure generation. The microelectrode (e.g., 10-100 micron electrodes with 100-500 micron spacing) arrays are used to continuously monitor the iEEG activity of sub-millimeter regions or islands (e.g., independent microdomains ~100-1000 micron diameter) throughout the epileptogenic zone of brain tissue and are combined with macroelectrodes (e.g., 1-5 mm diameter with 5-10 mm spacing) that provide large spatial scale information and can deliver electrical stimulation. The macroelectrode electrical stimulation allows direct modulation of the epileptic brain and neuronal populations comprising microdomain activity which is simultaneously monitored by microelectrode recordings. Macroelectrode stimulation is used to: 1.) Control microdomain and macroscale epileptiform activity, including but not limited to aborting microseizures, DC offsets, and high frequency local field oscillations by delivering stimulation that creates a counter field that exactly cancels the ongoing local field activity recorded from multiscale iEEG or stimulation paradigms that track rate of these biomarker events and adjust electrical stimulation to minimize their rates. Microwire electrode recordings are used to continuously monitor microdomain iEEG, multiunit, and single neuronal unit activity and are used to guide the feedback control signal from the macroelectrodes, 2.) Modulation of epileptic microdomains and measurement of the stimulus induced epileptiform activity of these regions to identify epileptic brain and states of increased seizure probability, i.e., the pre-ictal period. The generation of focal seizures results from the progressive coalescence of microseizure islands. The microseizures are precursor events to the onset of macroscale seizures, and cannot be detected by macroelectrodes or limited microwire recordings of the type used in the prior art and described above. Identified microseizures can be used alone or in combination with monitored pathological high-frequency epileptiform oscillations (pHFO). DC fluctuations and/or other parameters to identify periods where the brain is in a state of high seizure probability, and guide stimulation or other therapeutic interventions. Additionally, stimulation of regions of epileptic brain and simultaneous microdomain recordings can be used to identify regions of epileptic brain and to identify periods of increased probability of seizure occurrence.

A multiscale iEEG approach in accordance with one embodiment of the invention utilizes hybrid electrodes composed of microwire arrays that are combined with clinical macroelectrodes. This approach allows continuous recording of single neurons, small neuronal clusters, microdomains of the scale of cortical columns, as well as large-scale iEEG (macrodomain) activity, and permits stimulation (e.g., responsive, intermittent, or continuous) via standard clinical macroelectrodes. Research on patients undergoing evaluation for epilepsy surgery has produced identified electrographic signatures of epileptogenic brain and precursor events that herald the onset of seizures that are detectable using microelectrode arrays. By probing small spatial scales (~100-1000 um) seizure-like events, referred to as microseizures, have been identified on isolated sub-millimeter islands of brain. These microseizures are not detected on conventional macroelectrodes, but are clearly evident on adjacent microwire electrodes. Broadband recording from high spatial density microwire arrays (40 um wires with submillimeter spacing) show highly localized microseizures, high-frequency epileptiform oscillations (HFEO), and DC fluctuations that can effectively localize the epileptogenic zone and seizures. Prior to the onset of macroscale seizures recorded from clinical intracranial macroelectrodes (the macroscale seizures include clinical and subclinical seizure events), there is an increase in microseizure precursor events. The detection of these microseizure events can improve the efficacy of responsive brain stimulation and epilepsy surgery, and can be used to accurately forecast focal human seizures. For example, the delivery of an auditory tone or other warnings can be delivered to the patients when microseizure activity increases indicating an increased probability of seizure occurrence. Alternatively or in addition to the patient warnings, pre-emptive therapies (e.g., electrical stimulation and/or medications) can be delivered to the patient to mitigate or abort seizures before they fully develop.

These microscale seizure events are clinically silent, and so spatially localized that they are detectable on the microwire electrodes (e.g., 40 um in one embodiment) but not on the adjacent macroelectrodes. Microseizures demonstrate spectral characteristics, morphology and durations similar to electrographic seizures detected on macroelectrodes and often are precursors of macroscale seizures. Durations vary between 10 seconds and 10 minutes with a median of ~30 seconds. They are associated with an abrupt change in the background of the local microscale EEG and evolve in both amplitude and frequency; focal post-ictal spiking and slowing is also frequently observed. In general, the microseizures occur suddenly, and evolve in time and frequency. Less frequently the microseizures demonstrate spatial evolution and recruitment of surrounding seizure that can lead directly to a large scale seizure. Identification of these events can be by visual inspection or through automated detection algorithms. Microseizure data from hybrid depth, subdural strip and grid electrodes demonstrates an increase in the number of microseizures in epileptogenic brain compared to normal cortex and prior to macroelectrode seizures. The application of automated detectors to multiscale iEEG recordings of the type described herein demonstrates that the number of HFEO are significantly localized to the site of the seizure onset zone (SOZ). The microelectrodes show a bimodal distribution of HFEO frequencies with peaks in the ripple (80-250 Hz) and fast ripple (250-800 Hz) range. However, fast ripples were rarely recorded from the clinical macroelectrodes. Consistent with the results obtained using conventional iEEG, it has been determined that neocortical and medial temporal lobe onset seizures are associated with high frequency oscillations. In a study on 10 patients, 70% of seizures demonstrated high frequency oscillations at seizure onset. In the patients with microelectrodes within the seizure onset zone (4 medial temporal lobe patients, 4 neocortical patients), all demonstrated high frequency oscillations in the ripple or fast ripple range as seizure onset. Multiscale recording and stimulation approaches that probe the relevant spatial and temporal scales involved in the generation of seizures can improve the efficacy of responsive brain stimulation and epilepsy surgery. As is evident from the above discussion, by recording on spatial scales over which the emergence of seizures occur it is possible to identify microseizure precursor events that identify periods of increased probability of seizures and can anticipate the onset of macroscale seizures. Early spatiotemporal localization of seizures can enhance the success of responsive neurostimulation. By the time a seizure is detected using conventional macroelectrodes, a large mass of neural tissue may have been recruited and the seizure can be difficult to abort. The invention described above can be used: (1) for localization of epileptogenic brain zones, (2) for seizure forecasting and warning, (3) actively probing epileptic brain with electrical stimulation to localize the region of seizure onset and identify periods of increased seizure probability and/or (4) for seizure intervention. These applications can make use of continuous spatiotemporal profiles of microseizure events alone or in combination with high-frequency oscillations and/or DC fluctuations or by detecting the response of microdomain and macrodomain to electrical stimulation. In one embodiment macroelectrode stimulation of epileptogenic brain and detection of microdomain epiletiform activity, such as microseizures, spikes, DC shifts, or HFEO, is used to detect periods of increased probability of seizures. For example, continuous, time dependent probability distributions of the interictal signatures can be developed for: (1) number of occurrence, duration and spatial distribution of the events, (2) a sliding window over multiple temporal scales calculating the measures of the events, and/or (3) updating the probability of occurrence, duration of events and spatial distribution.

During localization of the epileptogenic zone (the EZ region of brain that is removed or lesioned in order to render a patient seizure free), the EZ can be mapped during chronic or intra-operative iEEG recordings to identify microseizures, HFEO and DC fluctuations. Statistical maps of signatures of these events can be co-registered to MRI. Statistically significant regions of increase in the events can then be identified.

Seizure forecasting and prediction can be warning of seizures occurring on a range of time scales (e.g., days, hours or seconds). The invention supports an increase in microseizure activity in the hours (e.g., about 2-6 hours) before clinical or subclinical electrographic seizures. Microseizures also directly progress into macroscale seizures on shorter temporal scales of minutes to seconds. The short-range time scale changes leading to seizure can be associated with: (1) the spread of microseizure activity to adjacent microelectrodes (spatial evolution), (2) increasing synchrony/correlation between microelectrodes EEG, and (3) increasing HFO (e.g., 70-1000 Hz) power present in the microelectrodes and macroelectrodes.

Probabilistic and threshold approaches can be used to determine the threshold level for triggering: (1) seizure warning, (2) intervention and/or (3) localization. A threshold can be determined from base-line non-seizure recording segments (including multiscale base-lines from course grained measures of months, weeks, days, hour and minutes, to fine grained measures of seconds). There can be a continuum of threshold levels that are associated with probability of seizure occurrence. The warning, intervention, or degree of localization can be a threshold at a fixed level or graded.

Based on the probability functions, a warning can be delivered to patients. The warning can be auditory (e.g., a beeper), visual (e.g., a flashing light), a warning to a PDA, broadcast to healthcare providers via a pager, or others.

Interventional stimulation can include electrical stimulation, focal drug delivery and/or focal cooling. Examples of electrical stimulation include real-time extracellular matrix voltage clamp to eliminate microseizures, simple repetitive pulse stimulation, and DC monopolar voltage to hyperpolarize the epileptogenic zone. Example of drugs that can be delivered include benzodiazepines, carbamezapine, lidocaine, ketamine, and others). In the event that a low probability of seizure occurrence is identified, no warning or intervention need be performed.

Extracellular voltage-clamp (ECVC) is a novel approach to altering the behavior of neural tissue by varying an electric field across a region of brain in such a way as to maintain a defined constant (DC) electric potential of the extracellular matrix at the site of a recording electrode, or group of electrodes. Doing so will alter the transmembrane potentials in this regions, moving the neurons further from, or closer to, their action potential firing thresholds. Care should be taken to limit current to acceptable safety margins, although these limits are not likely to be approached with this technique. Records of required correction, mirroring the ongoing, but nulled, field potentials, may be kept digitally as the cumulative sum of the applied voltages for therapeutic or diagnostic analysis. One approach is to apply stimulatory DC energy/field with a device located within a vein of the brain. That is, the stimulatory DC energy/field will be applied to brain tissue from across the venous vessel. Voltage clamping can be used in connection with the activity sensed on the microwire electrodes to vary the amount and/or duration of the voltage clamping.

Diagnostic stimulation protocols are for characterizing brain tissue and the monitoring of brain state and function. Stimulus protocols include, but are not limited to, pulse stimulation response (Valentin 2002), and continuous or intermittent wide bandwidth stimulus response measurements, including the linear response function impedance Z(J). Detection of stimulation response, including impedance, changes will be used for identifying pathologic brain (e.g. epileptogenic brain), changes in brain function and state (e.g. sleep/wake state, disease with paroxysmal cerebral dysfunction such as epilepsy, migraine, cerebral perfusion, stroke, trauma and encephalopathy are associated with impedance change). In particular, the invention includes the application of brain impedance monitoring for identifying time periods of increased probability of seizures in patients with epilepsy. The device can be utilized in patients with epilepsy for warning of impending seizures, or to initiate a therapeutic intervention to prevent seizure occurrence, but is not limited to this application. The approach applies to wide-bandwidth brain stimulation-response for impedance (linear-response) and higher order response terms measured from scalp, subgaleal, epidural, subdural, intraparenchymal or endovascular electrodes, or combination thereof.

The impedance Z(J) characterizes the linear response to injected time-varying current I(/), i.e. the voltage V(J)=Z(J) 1(J), and is the leading term in the Volterra series that describes the response, linear and non-linear response terms, to stimulation. White-noise stimulation currents that contain wide-bandwidth signal can be used to efficiently determine Z(J) across the frequency spectrum and are standard practice in engineering. Alternatively, the response at frequencies of interest can be obtained directly using sinusoidal stimulation. Any neurological event associated with changes in wide-bandwidth brain impedance could be identified and possibly anticipated with real-time continuous (or intermittent as needed) impedance monitoring. One implementation of this approach would be to seizure prediction, warning and intervention.

One embodiment of the invention uses a programmable wide-bandwidth stimulation-response protocol to determine brain impedance (and higher order terms if needed) with variable temporal resolution of impedances (e.g. 1 sec to multiple days). The preferred method achieves several advantages over previous methods reported to potential be useful seizure anticipation, such as:

Low computational complexity and minimal memory requirements;
  Frequency response, including impedance and higher order terms is easily obtained using current recording and stimulation technology;
  The algorithm is flexible and parameterized to allow the user to select optimally stimulation parameters (frequency, amplitude);
  The approach supports traditional thresholding-based decision making. The device operates on multiscale data from one or more scalp, subgaleal, epidural, subdural, intraparenchymal, endovascular electrodes, or a combination thereof. The device can incorporate multiscale electrodes of the type described herein delivered and placed in the brain by a venous approach.

It is understood here that "signal metadata" can be included to describe information that is not directly recorded by a sensor. Examples of signal metadata include, sleep/wake state which might originate from a separate sensor, or other device, including a medical device.

The device can be used to measure the response of a region of a patient's brain using wide-band stimulation. The linear-response (impedance and higher-order response terms from the stimulation are measured. The device includes a programmable stimulation subsystem for applying an electrical stimulation signal to a region of the brain. The stimulation can include wide bandwidth white noise and sinusoidal stimulation of variable frequency, but is not limited to these modalities. A sensing subsystem detects the response to the electrical stimulation and is coupled to a CPU and analysis module to calculate the frequency or other response signals. An output module initiates interventions or patient reporting. The device components can be enclosed in a biocompatible housing. Signal filtering can be performed on the data. The device allows for the user to program a range of frequency ranges of interest and the device can use the signal stimulation response as a feature to best identify changes in brain state and function of interest. The frequency response in the preferred embodiment may include, but is not limited to the following bands (upper/lower cutoff frequencies): (DC/0.1), (0.1/30), (30/80), (80/250), (250/1000), (1000/10,000). It is noted that many suitable filter bands have been identified in the neurological and signal processing literature, and may be employed in addition to, or alternatively to, those listed here. Similarly, a white noise signal containing all spectral components can be used for stimulation. Signal stimulation response feature extraction is applied to selected outputs. The specific signal stimulation-response features to be applied can be specified by a user interactively or in advance, or default values may be used, and in the preferred embodiment is the brain impedance. Classification of detected stimulation response events will be programmable to allow a range of classification schemes. Those skilled in the art will recognize that many different classifiers can be used, including kNN, decision trees, neural networks, svms, boosting, linear discriminant analysis. Further, those skilled in the art recognize that classifiers must be trained, and that the details of training, while straightforward, vary by classifier choice. Cortical electrodes currently utilized for diagnostic and therapeutic stimulation applications include subdural strip and grid electrodes. Multi-resolution or multiscale electrodes of the type described herein (e.g., containing a range of macroscale (~mm<2>) and microwire electrodes (~10<~3>mm)) can be deployed via the venous vasculature to neocortical sites of interest. Multiple endovascular electrodes can be deployed to approximate a grid array over large regions of neocortex.

Intraparenchymal depth electrodes are currently utilized for stimulation and recording of deep brain nuclei, hippocampus, cortical sulci, and deep cortex (e.g. insula and cingulate cortex). Multi-resolution endovascular electrodes can be implanted via the deep cerebral veins into all the above structures. Again, multiple multiresolution endovascular electrodes can be placed to approximate 1, 2, or even 3 dimensional arrays of electrodes for sensing and stimulating brain tissue.

Embodiments of a Multiresolution Endovascular Electrode System (MRES) (i.e., a multiscale electrode) in the venous vasculature which can, for example, be in the patient's brain. Other combinations of one or more microwire arrays and macro electrodes. The microwire electrode arrays W and macro electrodes M can also be positioned on other structures. For example, the MRES can include an expandable hollow cylinder of macroscale or macro electrodes M and microscale or microwire array W electrodes that is deployed within vessels of interest. Upon deployment the expanded hollow cylinder allows blood to flow through the cylindrical electrode. In end vessel venules the MRES may disrupt the vessel wall and occlude the flow of blood.

In some but not all embodiments of the MRES the microwire electrodes penetrate through the vessel wall, and the cylindrical electrode substrate compresses the sight of penetration, thus preventing bleeding. In yet another embodiment of the MRES the entire electrode is placed outside the vessel wall by allowing the catheter to exit the vessel and penetrating the brain to the site of interest and then deploying the electrode. With appropriate catheter dimensions, the venous vasculature can be used for access to brain regions within approximately 0.5-1 cm of all potential target sites using established endovascular guidance techniques. The electrode can, for example, be delivered over a previously positioned guide wire. Benefits to the venous approach include the following. The venous anatomy is fixed relative to the brain parenchyma allowing frameless procedures with accuracy equal or better than that afforded by stereotaxic frames. This will allow equivalent success in electrode placement with decreased patient discomfort, and decreased procedure times. Recovery times and hospital stays will be reduced. The prolonged immobility, and subcutaneous tunneling of electrodes required by standard procedures result in significant post-operative pain and recovery delays in many patients. The venous approach will require no period of immobility, and only a short segment of subcutaneous tunneling. Endovascular procedures carry less risk of infection. The majority of the length of the electrode will reside in the vascular system, subject to the patients immune system. Standard DBS electrodes proceed from a sub-galeal location to brain parenchyma, in minimal contact with the blood stream. Similarly, standard subdural and depth electrodes for used in the evaluation of intractable epilepsy are associate with increased risks of infection. Access via the venous system will result in lower risk of hemorrhage. By using the venous approach, the risk of arterial bleeding, present in standard DBS or epilepsy depth electrode procedures is completely averted. The low pressure of the venous system reduces the risk that any hemorrhage induced there will be difficult to control, and thus be of clinical significance.

Potential stimulation sites, therapeutic indications, and venous access points include the Hippocampus zone and the neocortex.

The subsystem of the device containing the power, logic and control components can be implanted in the subclavian space of the patient. Leads can extend from the subsystem through the patient's venous system (e.g., the jugular vein) to electrodes positioned at one or more zones of interest (e.g., seizure onset zones). The leads can branch into different veins, and one or more electrodes can be located at each of one or more locations. Stimulation and/or sensing electrodes of the types described above can be used with the device. The multiscale electrodes can be removed from the patient following procedures, or permanently placed in regions of the brain previously mapped and known to be a seizure onset zone. Brain activity such as microseizures can be sensed with the microwire array electrodes while therapeutic stimulation (e.g., traditional method, DC or voltage clamp) can be applied through the macro electrodes on the same or a different catheter carrier.

Although the present invention has been described with reference to preferred embodiments, those skilled in the art will recognize that changes can be made in form and detail without departing from the spirit and scope of the invention. In particular, the methods described herein can be implemented by wide variety of devices and systems, and can be used in connection with a wide variety of interventional therapies.

Tissue Impedance Measurement Technique: The technique for measuring tissue impedance is performed by passing an AC or DC stimulus current thru tissue between two or more electrodes and measuring the resulting voltage across the electrodes. Using Ohm's Law $R=E/I$ the impedance of the tissue is determined. For AC stimulus current the signal may be a complex waveform involving many frequencies and may include white noise waveforms for wide bandwidth frequency analysis of the impedance.

A Current Source used to generate the Stimulus Current is defined as an electronic circuit which will deliver a current with a constant magnitude and may be either a Direct Current source or an Alternating Current source in which the RMS current measurement remains constant even if the impedance of the medium experiences large impedance changes. The constant current source will adjust the applied voltage to maintain a consistent current flow.

Several electrode configurations may be used for the impedance measurements depending on the structure of brain being investigated and may include a single electrode between the patient's body tissue using a central distant point as the current return path and/or directly measured thru a small section of neural tissue using a pair of electrodes with the current being delivered differentially between the electrodes.

Differential current sources for multi-electrode/multi-site measurements using other configurations will be useful using a single electrode for the first differential current source terminal and several electrodes used as the second differential current source terminal. The resulting voltage would be measured between the terminals of the differential current source; between the first single electrode and the group of electrodes.

Because the tissue being tested will only tolerate a certain amount of cross-sectional current density level without damage due to heat dissipation or water molecule disassociation the maximum amount of current must be limited based on the surface area of the electrode (10s of microamps to nanoamps depending on the electrode geometry) the resulting voltage must be amplified and measured.

The device will also have the capability to measure multiple differential electrode implant sites to allow comparison between known good tissue and a suspected epilepsy focus area. This may be important to determine the probability of impending seizure by comparing changes in impedance of normal tissue to abnormal tissue. This will account for global changes in tissue impedance to improve the sensitivity of the analysis.

The current source test signal is generated with a voltage signal source driving/controlling a voltage to current converter electronic circuit. This allows several standard electronic circuit designs to be used for various signal waveform where applicable. Several voltage to current converter circuit designs may be used depending on the current magnitude and the amount of power available for the specific situation.

Tissue Stimulus Signal Generation: For very low power applications, such as in an implanted battery powered device, a very low power oscillator may be used to conserve power. This signal source would be controlled (on or standby) to only be operational when the measurements are needed.

A more flexible method for generating all types of waveforms will involve signal generation digitally using a microprocessor and a Digital to Analog converter. This will allow the possibility to generate all standard waveforms, frequency bandwidth limited noise or arbitrary waveforms.

Voltage to Current Source Circuits: A very simple circuit (figure xx) is a very energy efficient, small sized, method for generating a current source from a voltage signal. This involves using a fixed or variable resistor in series with the voltage source and the electrode. The resistor value must be much greater than the impedance of the specific electrode to avoid having differences in the tissue impedance imposing a significant error (or difference) in current signal from the test signal generation source. Normally this resistance is set to 1000 time the expected tissue impedance measurement but can be as low as 100 times the expected value.

A form of transistor based analog switch or multiplexer to select different resistance values for the current source to maintain a simple and very low power consumption circuit design to accommodate a large range of current source values may be used in some cases.

A multitude of active electronic circuits may be used for converting the voltage signal into a current source. These would be used for situations where the amount of power is not limited to battery operation and a wide range of current values are needed for various electrode geometries.

As described above, the tissue impedance can be determined by measuring the resulting voltage drop across the tissue when a known current signal is conducted thru the tissue. Using the measured voltage drop and the current source value the tissue impedance can be determined with the equation $Z=E/I$ or the measured voltage drop divided by the current source value.

There is a plurality of methods available to measure this voltage which include a direct high impedance voltage measurement device, an electronic circuit which includes a standard Operational Amplifier to buffer and amplify the voltage signal which may include driving one or more input channels of an Analog to Digital Converter based microprocessor or programmable logic based data acquisition system. In the latter case the same microprocessor may be used for signal generation, data acquisition, tissue impedance calculation, seizure probability increase warning/notification, and overall system timing and management.

The measurement configuration can include both single ended and differential voltage designs. If a single ended mode is used, this will involve using the "common large tissue connection for current source return point" mode, the significant stimulating and measurement electrode will be measured against the current return electrode.

The data acquisition rate of the resulting voltage must be at least twice the highest frequency component of the stimulation current signal, as per standard Nyquist signal sampling practices. We will normally use a 32 Khz per channel sampling rate per channel. If a lower frequency bandwidth is used a lower sampling rate may be used. The duration of the signal acquisition will be at least the duration of the stimulus current signal and may range from 10 milliseconds to several seconds. A baseline voltage signal may be measured before and after the stimulus current delivery to obtain the state of the tissue before and after stimulus delivery. The data measured before and after the stimulus delivery may be used to determine residual background signals of the brain and may be used to determine the voltage generated by the stimulus current signal.

The measured voltage signal measured across the tissue does not have to be stored but for early device/system development we will store waveforms to check for distortion and proper differential current source signal delivery. In an implantable device the measured signal does not have to be stored, only the resulting tissue impedance will need to be reported and/or saved.

Response Waveform Analysis: As previously mentioned the stimulus current signal may include: 1) simple direct current values; 2) simple sine wave signals of frequencies from 1 Hz to 10 Khz; and 3) complex waveforms with a combination of frequencies including a frequency bandwidth white noise signal.

For a direct current stimulus current stimulus signal the analysis will involve determining the tissue impedance using Ohms Law of $Z=E/I$.

The change in voltage can be measured during the stimulus delivery for significant changes during the stimulus delivery as the change in impedance may be significant in determining tissue state.

For a single frequency sine wave stimulus signal we will bandwidth pass filter the measured signal to avoid contamination of the resulting stimulus caused voltage signal from background noise and normal tissue generated signals of other frequencies than the stimulus current.

For complex multi frequency stimulus signals we will use standard frequency band analysis which may include standard Fast Fourier Transforms.

The resulting voltage signal analysis can be performed with software algorithms and may include: 1) standard frequency spectrum analysis such as FFT (Fast Fourier Transform), Wavelet Analysis, and/or Discrete TFD; 2) analysis of changes in the signal Frequency Spectrum including looking at both relative and absolute frequency band measures; and 3) correlation of changes in voltage signal Frequency Spectrum with the onset of patient seizures.

The analysis software algorithms are able to correlate changes in impedance across frequency and time. With standard software tools the strongly correlated specific measures to observed seizures will determine the set of measures that will be used for each patient can be easily determined. These specific measures of signal characteristics changes over time can then be programmed as parameters to the software algorithms to predict seizure onset and/or long term seizure probability.

This system has the capabilities to stimulate, measure and analyze tissue impedance at single and multiple frequencies thru the use of simple or complex waveforms. The proposed design also has the ability to detect changes in the impedance at single or multiple frequencies. Because the system can execute algorithms programmed into either the electronic circuitry or software algorithms, parameters and ranges of values can be selected which correlate with seizure onset.

Once the signal component characteristic measurements are determined as reliable predictors for a specific patient (or tissue area) these parameters/values will be load into the devices memory and used to predict seizure onset.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products. Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A brain electrode device comprising:
one or more macroelectrodes;
a respective plurality of microelectrodes encompassed within each macroelectrode of the one or more macroelectrodes, wherein each microelectrode of the respective plurality of microelectrodes and each macroelectrode of the one or more macroelectrodes is electrically isolated; and
a respective plurality of additional electrodes within each macroelectrode of the one or more macroelectrodes,
wherein each additional electrode of the respective plurality of additional electrodes is larger than each microelectrode of the respective plurality of microelectrodes,
wherein the respective plurality of additional electrodes within each macroelectrode of the one or more macroelectrodes includes a respective first subset of additional electrodes having a first size and a respective second subset of additional electrodes having a second size larger than the first size,
wherein the respective plurality of microelectrodes surround the respective first subset of additional electrodes according to a first iteration of a fractal pattern and the respective first subset of additional electrodes surround the respective second subset of additional electrodes according to a second iteration of the fractal pattern.

2. The brain electrode device of claim 1, wherein the one or more macroelectrodes comprise at least two macroelectrodes.

3. The brain electrode device of claim 1, wherein the brain electrode device is configured for permanent implantation in contact with a brain of a human patient.

4. The brain electrode device of claim 1, wherein the one or more macroelectrodes comprise at least ten macroelectrodes.

5. The brain electrode device of claim 1, wherein the plurality of microelectrodes encompassed within each macroelectrode comprises at least 16 microelectrodes.

6. The brain electrode device of claim 1, wherein the respective second subset of additional electrodes surround a central electrode of the macroelectrode according to a third iteration of the fractal pattern, the central electrode having a third size larger than the second size.

7. A method of stimulating and mapping activity of a brain of a human patient, the method comprising:
coupling a brain electrode device to the patient such that the brain electrode device can detect EEGs of the brain, wherein the brain electrode device comprises:
one or more macroelectrodes;
a respective plurality of microelectrodes encompassed within each macroelectrode of the one or more macroelectrodes, wherein each microelectrode of the respective plurality of microelectrodes and each macroelectrode of the one or more macroelectrodes is electrically isolated; and
a respective plurality of additional electrodes within each macroelectrode of the one or more macroelectrodes,
wherein each additional electrode of the respective plurality of additional electrodes is larger than each microelectrode of the respective plurality of microelectrodes,
wherein the respective plurality of additional electrodes within each macroelectrode of the one or more macroelectrodes includes a respective first subset of additional electrodes having a first size and a respective second subset of additional electrodes having a second size larger than the first size,
wherein the respective plurality of microelectrodes surround the respective first subset of additional electrodes according to a first iteration of a fractal pattern and the respective first subset of additional electrodes surround the respective second subset of additional electrodes according to a second iteration of the fractal pattern;
providing an electrical stimulation to the brain from the one or more macroelectrodes; and
after providing the electrical stimulation, detecting, using the plurality of microelectrodes, micro-EEGs from the brain.

8. The method of claim 7, further comprising recording EEGs from the brain using the one or more macroelectrodes.

9. The method of claim 7, further comprising determining, based on the micro-EEGs, that the patient is having micro-seizures.

10. The method of claim 9, further comprising determining, based on the determining that the patient is having micro-seizures, one or more seizure loci.

11. The method of claim 7, further comprising determining one or more loci based on determining the patient is having one of more of: (i) changes in pathological biomarkers recorded on the brain electrode device, (ii) micro epileptiform discharges, (iii) pathological high frequency oscillations, (iv) focal slow-wave oscillations, (v) micro DC-shifts, and (vi) micro-seizures.

12. The method of claim 7, wherein the respective second subset of additional electrodes surround a central electrode of the macroelectrode according to a third iteration of the fractal pattern, the central electrode having a third size larger than the second size.

13. A brain electrode device for recording electrical and magnetic fields, the device comprising:
one or more macroelectrodes and magnetometers;
a respective plurality of microelectrodes encompassed within each macroelectrode of the one or more macroelectrodes, wherein each microelectrode of the respective plurality of microelectrodes and each macroelectrode of the one or more macroelectrodes is electrically isolated; and
a respective plurality of additional electrodes within each macroelectrode of the one or more macroelectrodes,
wherein each additional electrode of the respective plurality of additional electrodes is larger than each microelectrode of the respective plurality of microelectrodes,
wherein the respective plurality of additional electrodes within each macroelectrode of the one or more macroelectrodes includes a respective first subset of additional electrodes having a first size and a respective second subset of additional electrodes having a second size larger than the first size,
wherein the respective plurality of microelectrodes surround the respective first subset of additional electrodes according to a first iteration of a fractal pattern and the respective first subset of additional electrodes surround the respective second subset of additional electrodes according to a second iteration of the fractal pattern.

14. The brain electrode device of claim 13, wherein the respective second subset of additional electrodes surround a central electrode of the macroelectrode according to a third iteration of the fractal pattern, the central electrode having a third size larger than the second size.

15. A system comprising:
one or more multiscale electrodes configured and operable for (i) actively probing, (ii) passively recording, and (iii) measuring biomarkers including at least one of the group including interictal spikes, high frequency oscillations, focal slow oscillations, focal DC shifts, and microseizures, the one or more multiscale electrodes comprising:
one or more macroelectrodes;
a respective plurality of microelectrodes encompassed within each macroelectrode of the one or more macroelectrodes, wherein each microelectrode of the respective plurality of microelectrodes and each macroelectrode of the one or more macroelectrodes is electrically isolated; and
a respective plurality of additional electrodes within each macroelectrode of the one or more macroelectrodes,
wherein each additional electrode of the respective plurality of additional electrodes is larger than each microelectrode of the respective plurality of microelectrodes,
wherein the respective plurality of additional electrodes within each macroelectrode of the one or more macroelectrodes includes a respective first subset of additional electrodes having a first size and a respective second subset of additional electrodes having a second size larger than the first size,
wherein the respective plurality of microelectrodes surround the respective first subset of additional electrodes according to a first iteration of a fractal pattern and the respective first subset of additional electrodes surround the respective second subset of additional electrodes according to a second iteration of the fractal pattern; and
a computer processing system configured and operable for:
analyzing multi-scale electrophysiological data acquired from the one or more multiscale electrodes; and
mapping an epileptogenic brain using the multi-scale electrophysiological data acquired from the one or more multiscale electrodes.

16. The system of claim 15, wherein the biomarkers are measured on micro-scales during an interictal state.

17. The system of claim 16, wherein the interictal state is during intraoperative or during pharmacological interventions.

18. The system of claim 15, wherein the respective second subset of additional electrodes surround a central electrode of the macroelectrode according to a third iteration of the fractal pattern, the central electrode having a third size larger than the second size.

* * * * *

UNITED STATES PATENT AND TRADEMARK OFFICE
CERTIFICATE OF CORRECTION

PATENT NO. : 12,193,825 B2
APPLICATION NO. : 17/544782
DATED : January 14, 2025
INVENTOR(S) : Benjamin H. Brinkmann, Squire M. Stead and Gregory A. Worrell It is certified that error appears in the above-identified patent and that said Letters Patent is hereby corrected as shown below:

In the Specification

In Column 1, Line 15 (Approx.), delete "are application are" and insert --are--.

In Column 1, Line 16 (Approx.), after application insert --.--.

Signed and Sealed this
Fourth Day of March, 2025

Coke Morgan Stewart
*Acting Director of the United States Patent and Trademark Office*